United States Patent
Goldstein et al.

(10) Patent No.: US 6,943,184 B2
(45) Date of Patent: Sep. 13, 2005

(54) 1,1- AND 1,2-DISUBSTITUTED CYCLOPROPANE COMPOUNDS

(75) Inventors: Solo Goldstein, Suresnes (FR); Claude Guillonneau, Clamart (FR); Yves Charton, Sceaux (FR); Brian Lockhart, Croissy sur Seine (FR); Pierre Lestage, La Celle Saint Cloud (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 336 days.

(21) Appl. No.: 09/888,990

(22) Filed: Jun. 26, 2001

(65) Prior Publication Data

US 2002/0022643 A1 Feb. 21, 2002

(30) Foreign Application Priority Data

Jun. 27, 2000 (FR) .......................................... 00 08203

(51) Int. Cl.[7] ...................... A61K 31/44; C07D 213/00
(52) U.S. Cl. ...................................... 514/351; 546/300
(58) Field of Search ........................... 546/300; 514/351

(56) References Cited

PUBLICATIONS

Neuropsychopharmacology, 22, 461–565 (2000).
Cur. Med. Chemistry, 8, 651–674 (2001).
Jpn. J. Pharmacol., 88, 133–138 (2002).
J. Pharm. Exp. Ther., 292, 461–467 (2000).
Psychopharmacology, 138, 217–230 (1998).
Psychopharmacology, 143, 158–165 (1999).
Dementia, 7, 47–52 (1996).
Am. J. Psychiatry, 160, 1856–1861 (1993).
Biol. Psychiatry, 32, 607–616 (1992).
Biol. Psychiatry. 44, 98–106 (1998).
Psychopharmacology, 123, 55–63 (1996).
Neuroreport, 9, 57–60 (1998).
Drug Dev. Res., 38, 290–298 (1996).
Brain Res. Bull., 57, 133–150 (2002).
J. Pharm. Exp. Ther., 295, 321–327 (2000).

*Primary Examiner*—Celia Chang
(74) *Attorney, Agent, or Firm*—The Firm of Hueschen and Sage

(57) ABSTRACT

A compound selected from those of formula (I):

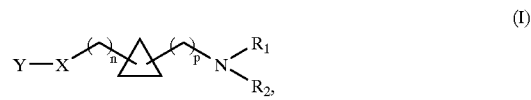

wherein:
p represents an integer of from 0 to 6 inclusive,
n represents an integer of from 0 to 6 inclusive,
$R_1$, and $R_2$ represent a group selected from hydrogen, alkyl, aryl and arylalkyl, or $R_1+R_2$ form together with nitrogen carrying them saturated, monocyclic, or bicyclic system,
X represents a group selected from oxygen, sulphur, a group —CH=CH—, methylene, a group of formula —HC=N—O— and a group of formula —O—CH$_2$—CH=CH—, in which groups oxygen is linked to Y of the compounds of formula (I),
Y represents a group selected from aryl, heteroaryl, arylalkyl, heteroarylalkyl, —C(O)-A, and —C(S)-A,
A represents a group selected from alkyl, aryl, heteroaryl, arylalkyl, heteroarylalkyl, and $NR_3R_4$ wherein $R_3$, and $R_4$ represent a group selected from hydrogen, alkyl, aryl, and arylalkyl, or $R_3+R_4$ form together with nitrogen carrying them monocyclic, or bicyclic ($C_3$–$C_{10}$) system,
its isomers and addition salts thereof with a pharmaceutically-acceptable acid or base, and medicinal products containing the same which are useful as specific nicotinic ligand of $\alpha_4\beta_2$ receptors.

12 Claims, No Drawings

1,1- AND 1,2-DISUBSTITUTED CYCLOPROPANE COMPOUNDS

FIELD OF THE INVENTION

The present invention relates to new 1,1- and 1,2-disubstituted cyclopropane compounds, and to pharmaceutical compositions containing them.

The compounds of the present invention are especially valuable from a pharmacological point of view because of their specific interaction with central nicotinic receptors of type α4β2, having application in the treatment of neuropathologies associated with cerebral ageing, of mood disorders, of pain and of tobacco withdrawal.

Ageing of the population due to increased life expectancy at birth has brought with it a major increase in the incidence of age-related neuropathologies and especially of Alzheimer's disease. The principal clinical manifestations of cerebral ageing and especially of age-related neuropathologies are deficiencies in mnemic and cognitive functions, which may lead to dementia. It has been widely demonstrated that, of the various neuro-transmitters, acetylcholine plays a major role in memory functions and that there is large-scale destruction of the cholinergic neuronal pathways in certain neurodegenerative diseases or when there is inadequate activation in the case of cerebral ageing. For that reason, numerous therapeutic approaches have been aimed at preventing destruction of the neurotransmitter by means of the inhibition of acetylcholinesterase or have sought to provide a substitute for the deficient neurotransmitter. In the latter case, the cholinergic agonists proposed have been of the muscarinic type, which are specific for post-synaptic M1 receptors.

It has recently been shown that the cholinergic impairment associated with Alzheimer's disease affects neurones carrying nicotinic receptors more than those carrying muscarinic receptors (Schroder et al., "Alzheimer disease: therapeutic strategies", Birkhauser Boston, 1994, 181–185). Numerous studies have, moreover, demonstrated that nicotine has memory-facilitating properties (Prog. Neuropsychopharmacol., 1992, 16, 181–191) and that these properties are exerted as much on mnemic functions (Psychopharmacol., 1996, 123, 88–97) as on the faculties of attention and vigilance (Psychopharmacol., 1995, 118, 195–205). Furthermore, nicotine exerts neuroprotective effects with respect to excitotoxic agents such as glutamate (Brain Res., 1994, 644, 181–187).

All of these findings can very probably be linked with epidemiological studies which have shown a lower incidence of Alzheimer's disease and Parkinson's disease in smokers. Furthermore, several studies have shown the value of nicotine in the treatment of mood disorders such as states of depression, anxiety or schizophrenia. Finally, it has been shown that nicotine has antalgic properties. All of the therapeutic properties of nicotine and also those described for other nicotinic agents are based upon activity with respect to central receptors, which differ structurally and pharmacologically from peripheral receptors (muscle and ganglion). The central receptors of type α4β2 are the most represented in the central nervous system and have been implicated in the majority of the therapeutic effects of nicotine (Life Sci., 1995, 56, 545–570).

PRIOR ART DESCRIPTION

Several documents such as Synlett., 1999, 7, 1053–1054; J. Med. Chem., 1985, 28(12), 1953–1957 and 1980, 23(3), 339–341; 1970, 13(5), 820–826; 1972, 15(10), 1003–1006; J. Am. Chem. Soc., 1987, 109(13), 4036–4046, or a few patents or patent applications such as DE 36 08 727, EP 124 208 or WO 94/10158 describe and claim compounds containing a 1,1- or 1,2-disubstituted cyclopropane moiety. None of those references describe or suggest that those compounds have pharmacological activity that is specific for nicotinic receptors and more especially for central nicotinic receptors of type α4β2, this being a novel property of the compounds described by the Applicant. Consequently, there is nothing in the prior art predicting the specific and surprising characteristics of the products claimed in the present Application.

The compounds of the present invention are therefore new and represent powerful selective nicotinic ligands of the central receptor sub-type α4β2. They are consequently of use in the treatment of deficiencies of memory associated with cerebral ageing and with neurodegenerative diseases such as Alzheimer's disease, Parkinson's disease, Pick's disease, Korsakoff's disease and frontal lobe and subcortical dementias, and also for the treatment of mood disorders, Tourette's syndrome, hyperactivity syndrome with attention-deficit, tobacco withdrawal and pain.

DETAILED DESCRIPTION OF THE INVENTION

More specifically, the present invention relates to compounds of formula (I):

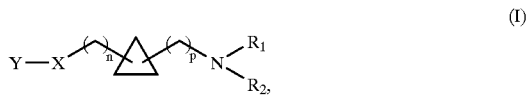

wherein:

p represents an integer of from 0 to 6 inclusive, n represents an integer of from 0 to 6 inclusive, $R_1$ and $R_2$, which may be identical or different, each independently of the other represent a group selected from a hydrogen atom, a linear or branched $(C_1-C_6)$alkyl group, an aryl group and an aryl-$(C_1-C_6)$alkyl group in which the alkyl moiety is linear or branched, or $R_1+R_2$ form together with the nitrogen atom carrying them a saturated, 3- to 10-membered, monocyclic or bicyclic system optionally containing a second hetero atom selected from oxygen, nitrogen and sulphur, X represents a group selected from an oxygen atom, a sulphur atom, a group —CH=CH—, methylene, a group of formula —HC=N—O— and a group of formula —O—CH$_2$—CH=CH—, in which groups the oxygen atom is linked to the Y moiety of the compounds of formula (I), Y represents a group selected from aryl, heteroaryl, aryl-$(C_1-C_6)$alkyl in which the alkyl moiety is linear or branched, heteroaryl-$(C_1-C_6)$alkyl in which the alkyl moiety is linear or branched, —C(O)-A and —C(S)-A, A represents a group selected from linear or branched $(C_1-C_6)$alkyl, aryl, heteroaryl, aryl-$(C_1-C_6)$alkyl in which the alkyl moiety is linear or branched, heteroaryl-$(C_1-C_6)$alkyl in which the alkyl moiety is linear or branched, and $NR_3R_4$ wherein $R_3$ and $R_4$, which may be identical or different, each represent a group selected from a hydrogen atom, a linear or branched $(C_1-C_6)$alkyl group, an aryl group and an aryl-$(C_1-C_6)$alkyl group in which the alkyl moiety is linear or branched, or $R_3+R_4$ form together with the nitrogen atom carrying them a monocyclic or bicyclic $(C_3-C_{10})$ system, their isomers and addition salts thereof with a pharmaceutically acceptable acid or base, with the proviso that:

in the case of 1,1-disubstituted compounds of formula (I), p is other than zero when X represents a methylene group, n has the value zero, Y represents an aryl or heteroaryl group, and $R_1$ and $R_2$, which may be identical or different, represent a hydrogen atom, a linear or branched ($C_1$–$C_4$) alkyl group, a benzyl group, a phenylethyl group, or form together with the nitrogen atom carrying them a morpholino group, a thiomorpholino group or a 5- to 7-membered saturated carbocyclic system, p is other than zero when X represents a methylene group, n has the value zero, Y represents an acetyl group, and $R_1$ and $R_2$, which may be identical or different, represent a hydrogen atom, a linear or branched ($C_1$–$C_4$)alkyl group, a phenyl group, a benzyl group, or form together with the nitrogen atom carrying them a piperidyl or morpholino group, $R_1$ and $R_2$ do not simultaneously represent a methyl group:
   either when p and n each have the value 1, X represents an oxygen atom and Y represents a group selected from p-nitrobenzoyl, p-aminobenzoyl, p-chlorophenylaminocarbonyl, and acetyl,
   or when p has the value zero, n has the value 1, X represents an oxygen atom or a sulphur atom and Y represents a 2-quinolyl group substituted in the 3-position by a linear or branched ($C_3$–$C_4$)alkyl group, or a phenyl group, Y does not represent a 1,2-benzisoxazol-3-yl group when n has the value 1, p has the value zero and X represents an oxygen atom, in the case of 1,2-disubstituted compounds of formula (I), $R_1$ and $R_2$ do not simultaneously represent a hydrogen atom when p and n each have the value zero and X-Y together represent a phenoxy group (optionally substituted by one or two identical or different groups selected from methoxy, dimethylamino, halogen, methyl, trifluoromethyl, nitro and amino), a phenylsulphanyl group, a benzyloxy group, a benzyl group or a 2-phenylethyl group, $R_1$ and $R_2$ do not simultaneously represent a methyl group when p and n each have the value zero and X-Y together represent a phenoxy group (optionally substituted by a group selected from a chlorine atom, and trifluoromethyl), a phenylsulphanyl group or a benzyl group, and also with the proviso that the compounds of formula (I) are other than the following compounds:

(1-benzylcyclopropyl)methanamine,
(1-benzylcyclopropyl)-N,N-dimethylmethanamine,
2-(phenoxycyclopropyl)methanamine,
2-(phenoxymethyl)-cyclopropanamine,
(N,N-dimethyl)-2-(acetoxymethyl)-cyclopropanemethanamine,
N-{2-[2-(benzyloxy)ethyl]cyclopropyl}-N,N-dimethylamine.

An aryl group denotes a phenyl, biphenyl, naphthyl, dihydronaphthyl, tetrahydronaphthyl, indanyl or indenyl group, each of those groups being optionally substituted by one or more identical or different groups selected from halogen atoms, linear or branched ($C_1$–$C_6$)alkyl, hydroxy, cyano, nitro, linear or branched ($C_1$–$C_6$)alkoxy, linear or branched ($C_2$–$C_7$)acyl, linear or branched ($C_1$–$C_6$) alkoxycarbonyl, linear or branched ($C_1$–$C_6$)trihaloalkyl, linear or branched ($C_1$–$C_6$)trihaloalkoxy groups and amino groups optionally substituted by one or two linear or branched ($C_1$–$C_6$)alkyl groups.

A heteroaryl group denotes a 5- to 12-membered, monocyclic aromatic or bicyclic system containing from one to three identical or different hetero atoms selected from oxygen, nitrogen and sulphur, one of the rings of which, in the case of a bicyclic system, is aromatic in character, and the other ring of which may be aromatic or partially hydrogenated, each of those groups being optionally substituted by one or more identical or different groups selected from the substituents defined hereinbefore for an aryl group.

In general, the 1,1-disubstituted and 1,2-disubstituted compounds relate to compounds having a moiety

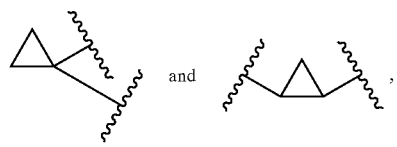

respectively.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Preferred compounds of the invention are those compounds wherein n is an integer of from 0 to 2 inclusive.

Advantageously, preferred compounds of the invention are those compounds wherein p is an integer having the value 0 or 1.

The substituents $R_1$ and $R_2$ that are preferred according to the invention are the hydrogen atom and the linear or branched ($C_1$–$C_6$)alkyl group.

The substituent X that is preferred according to the invention is the oxygen atom.

The substituents Y that are preferred according to the invention are groups selected from —C(O)NR$_3$R$_4$ wherein $R_3$ and $R_4$ are as defined for formula (I), acetyl, —C(O)-heteroaryl, aryl-($C_1$–$C_6$)alkyl in which the alkyl moiety is linear or branched, and heteroaryl. Advantageously, the preferred heteroaryl group in the definitions of Y is the pyridyl group.

According to an advantageous embodiment of the invention, preferred compounds are 1,1-disubstituted compounds of formula (I) corresponding to formula (IA):

(IA)

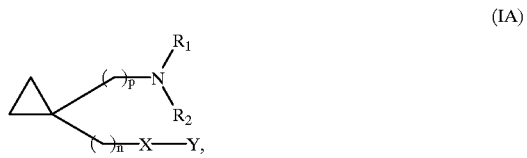

wherein n, p, X, Y, $R_1$ and $R_2$ are as defined for formula (I).

According to another advantageous embodiment of the invention, preferred compounds are 1,2-disubstituted compounds of formula (I) corresponding to formula (IB):

(IB)

wherein n, p, X, Y, $R_1$ and $R_2$ are as defined for formula (I).

In especially advantageous manner, preferred compounds of the invention are compounds of formula (IB) wherein p represents 0 or 1, n represents 0 or 1, $R_1$ and $R_2$, which may be identical or different, represent a hydrogen atom or a linear or branched ($C_1$–$C_6$)alkyl group, X represents an oxygen atom, and Y represents a group selected from phenyl-($C_1$–$C_6$)alkyl in which the alkyl moiety is linear or branched, pyridyl and —C(O)-A wherein A represents a linear or branched ($C_1$–$C_6$)alkyl group, mono($C_1$–$C_6$) alkylamino or di($C_1$–$C_6$)alkylamino, the alkyl moiety (moieties) being linear or branched.

In another very advantageous manner, preferred compounds of the invention are compounds of formula (IA) wherein p represents 0 or 1, n is an integer of from 0 to 3 inclusive, $R_1$ and $R_2$, which may be identical or different, represent a hydrogen atom, a linear or branched ($C_1$–$C_6$) alkyl group or form together with the nitrogen atom carrying them a pyrrolidinyl radical, X represents an oxygen atom, a sulphur atom or a group —CH=CH—, and Y represents a group selected from phenyl (optionally substituted by a hydroxy group, a linear or branched ($C_1$–$C_6$)alkyl group or a halogen atom), pyridyl, pyridyl-($C_1$–$C_6$)alkyl in which the alkyl moiety is linear or branched (the pyridyl radical in each of those groups being optionally substituted by a group selected from a halogen atom and a linear or branched ($C_1$–$C_6$)alkyl group), and —C(O)-A wherein A represents a group selected from linear or branched ($C_1$–$C_6$)alkyl, linear or branched mono($C_1$–$C_6$)alkylamino, linear or branched di($C_1$–$C_6$)alkylamino, and pyridyl.

In especially advantageous manner, preferred compounds of the invention are:
2-[1-(dimethylamino)cyclopropyl]ethyl methylcarbamate,
2-[1-(dimethylamino)cyclopropyl]ethyl dimethylcarbamate,
[1-(dimethylamino)cyclopropyl]methyl dimethylcarbamate,
[1-(dimethylamino)cyclopropyl]methyl acetate,
2-[1-(dimethylamino)cyclopropyl]ethyl acetate,
1-[(dimethylamino)methyl]cyclopropyl acetate,
[1-(dimethylamino)cyclopropyl]methyl nicotinate,
N,N-dimethyl-1-[(3-pyridyloxy)methyl]cyclopropanamine,
N-methyl-1-[(3-pyridyloxy)methyl]cyclopropanamine,
N,N-dimethyl-1-[(3-pyridylmethoxy)methyl] cyclopropanamine,
N,N-dimethyl-1-[2-(3-pyridyloxy)ethyl]cyclopropanamine,
4-({2-[1-dimethylamino)cyclopropyl]ethyl}sulphanyl) phenol,
(±)-cis-2-(dimethylamino)cyclopropyl methylcarbamate,
(±)-trans-2-(dimethylamino)cyclopropyl methylcarbamate,
(±)-cis-2-(dimethylamino)cyclopropyl acetate,
(±)-trans-2-(dimethylamino)cyclopropyl acetate,
(±)-cis-2-(dimethylamino)cyclopropyl]methyl acetate,
(±)-trans-2-(dimethylamino)cyclopropyl]methyl acetate,
(±)-cis-2-[(benzyloxy)methyl]-N,N-dimethylcyclopropanamine,
(±)-trans-2-[(benzyloxy)methyl]-N,N-dimethylcyclopropanamine,
(±)-trans-2-[(dimethylamino)methyl]cyclopropyl acetate,
1-[(3-pyridyloxy)methyl]cyclopropanamine dihydrochloride,
N-methyl-1-{[(6-methyl-3-pyridyl)oxy] methyl}cyclopropanamine hydrochloride,
N-methyl-1-{[(6-chloro-3-pyridyl)oxy] methyl}cyclopropanamine hydrochloride,
N-{1-[(3-fluorophenoxy)methyl]cyclopropyl}-N-methylamine hydrochloride,
3-[1-(dimethylamino)cyclopropyl]propyl dimethylcarbamate fumarate,
3-[1-(dimethylamino)cyclopropyl]propyl methylcarbamate fumarate,
N-methyl-1-[(2-pyridylsulphanyl)methyl] cyclopropanamine dihydrochloride,
N-methyl-1-[3-(3-pyridyloxy)propyl]cyclopropanamine dihydrochloride,
N-methyl-1-[2-(3-pyridyl)ethyl]cyclopropanamine dihydrochloride,
N-methyl-1-[(Z)-2-(3-pyridyl)ethenyl]cyclopropanamine fumarate,
[1-(1-pyrrolidinyl)cyclopropyl]methyl dimethylcarbamate fumarate,
N,N-dimethyl-1-[2-(3-pyridyl)ethyl]cyclopropanamine hydrochloride,
3-{[1-(1-pyrrolidinyl)cyclopropyl]methoxy}pyridine fumarate,
N-methyl-1-[2-(3-pyridyloxy)ethyl]cyclopropanamine fumarate,
2-[1-(methylamino)cyclopropyl]ethyl dimethylcarbamate hydrochloride, and
2-[1-(1-pyrrolidinyl)cyclopropyl]ethyl dimethylcarbamate fumarate.

The isomers, as well as the addition salts with a pharmaceutically acceptable acid or base, of the preferred compounds form an integral part of the invention.

The present invention relates also to a process for the preparation of compounds of formula (I), which process is characterised in that there is used as starting material a compound of formula (II):

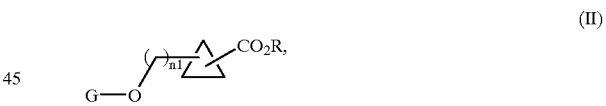
(II)

wherein G represents a protecting group for hydroxy functions that is conventionally used in organic synthesis, R represents a hydrogen atom or a linear or branched ($C_1$–$C_6$) alkyl group, and $n_1$ represents 0 or 1, which compounds of formula (II) are:
either reacted with liquid ammonia in the presence of an alkali metal cyanide in an alcoholic solvent to yield the compounds of formula (III):

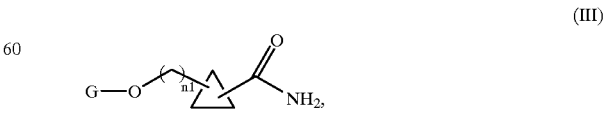
(III)

wherein G represents a protecting group for hydroxy functions and n, represents 0 or 1, which compounds of formula (III) are treated with a dihalide in the presence of a base such as sodium hydroxide to yield the compounds of formula (IV):

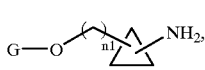
(IV)

wherein G and $n_1$ are as defined hereinbefore, the primary amine function of which compounds of formula (IV) is selectively protected by a protecting group $G_2$ customarily used in organic chemistry such as the group BOC (t-butoxycarbonyl) to yield the compounds of formula (V):

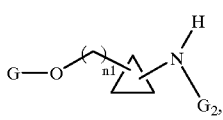
(V)

wherein $n_1$, G and $G_2$ are as defined hereinbefore, which compounds of formula (V) are then successively:

treated, in a basic medium, with a compound of formula (VIA):

$R_1$-$L_1$ (VIA), wherein $R_1$ is as defined for formula (I) and $L_1$ represents a customary leaving group of organic synthesis, the amine function of which is then deprotected, which compounds either undergo no further treatment and consequently yield compounds of formula (VIIA):

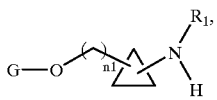
(VIIA)

wherein $R_1$, $n_1$ and G are as defined hereinbefore, or are reacted with a compound of formula (VIB):

$R_{2a}$-$L_1$ (VIB), wherein $R_{2a}$ has the same meanings as $R_2$ as defined for formula (I) except for the meaning of a hydrogen atom and $L_1$ is as defined hereinbefore, to yield compounds of formula (VIIB):

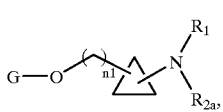
(VIIB)

wherein $R_1$, $R_{2a}$, $n_1$ and G are as defined hereinbefore, the totality of the compounds of formulae (VIIA) and (VIIB) forming the compounds of formula (VII):

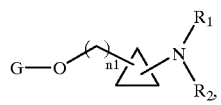
(VII)

wherein $n_1$, G, $R_1$ and $R_2$ are as defined hereinbefore, the hydroxy function of which compounds of formula (VII) is deprotected, which compounds are then:

either treated with a compound of formula (VIII):

Y-$L_1$ (VIII), wherein Y is as defined for formula (I) and $L_1$ is as defined hereinbefore, to yield compounds of formula (I/a), a particular case of the compounds of formula (I):

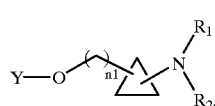
(I/a)

wherein $n_1$, Y, $R_1$ and $R_2$ are as defined for formula (I), or reacted with $SOCl_2$ to yield compounds of formula (IX):

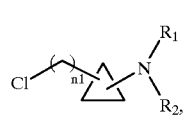
(IX)

wherein $n_1$, $R_1$ and $R_2$ are as defined hereinbefore, which compounds of formula (IX) are reacted, in a basic medium, with a compound of formula (X):

$Y_1$—SH (X), wherein $Y_1$ represents an aryl group, an aryl-($C_1$–$C_6$)alkyl group in which the alkyl moiety is linear or branched, a heteroaryl group or a heteroaryl-($C_1$–$C_6$)alkyl group in which the alkyl moiety is linear or branched, to yield compounds of formula (I/b), a particular case of the compounds of formula (I):

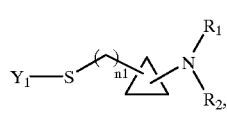
(I/b)

wherein $Y_1$, $n_1$, $R_1$ and $R_2$ are as defined hereinbefore, or, when $n_1$ has the value 1, subjected to the action of a conventional oxidising agent of organic synthesis to yield compounds of formula (XI):

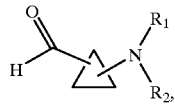

(XI)

wherein $R_1$ and $R_2$ are as defined hereinbefore, which compounds of formula (XI) are:
either treated with a hydroxylamine of formula (XII):

(XII), wherein $Y_2$ represents a hydrogen atom or a group $Y_1$ as defined hereinbefore, to yield compounds of formula (I/c), a particular case of the compounds of formula (I):

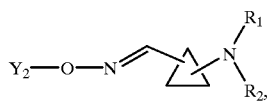

(I/c)

wherein $Y_2$, $R_1$ and $R_2$ are as defined hereinbefore, which compounds of formula (I/c), in the particular case where $Y_2$ represents a hydrogen atom, are subjected to the action of a compound of formula (XIV):

(XIV), wherein $L_1$ is as defined hereinbefore and $Y_3$ represents a group of formula —C(O)-A or —C(S)-A as defined for formula (I), to yield compounds of formula (I/d), a particular case of the compounds of formula (I):

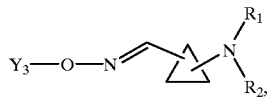

(I/d)

wherein $Y_3$, $R_1$ and $R_2$ are as defined hereinbefore,
or treated under Wittig reaction conditions and then subjected to the action of a customary reducing agent of organic synthesis to yield compounds of formula (I/e), a particular case of the compounds of formula (I),

(I/e)

wherein $Y_1$, $R_1$ and $R_2$ are as defined hereinbefore,
or subjected to the action of a compound of formula $Ph_3P=CH-CO_2Et$ and then reduced by the action of a reducing agent of organic synthesis to yield compounds of formula (XV):

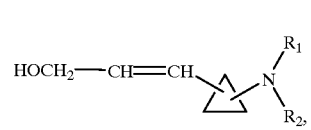

(XV)

wherein $R_1$ and $R_2$ are as defined hereinbefore, which compounds of formula (XV) are treated with a compound of formula (VIII) as defined hereinbefore to yield compounds of formula (I/f), a particular case of the compounds of formula (I):

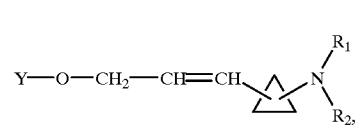

(I/f)

wherein Y, $R_1$ and $R_2$ are as defined for formula (I),
or, when $n_1$ has the value 1, converted into their corresponding halogenated derivative under customary conditions of organic chemistry and then reacted with an alkali metal cyanide in the presence of dimethyl sulphoxide to yield compounds of formula (XVI):

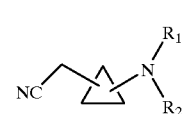

(XVI)

wherein $R_1$, $R_2$ are as defined hereinbefore, which compounds of formula (XVI) are converted into an ester under conventional conditions and then subjected to a reducing agent to yield compounds of formula (XVIIA):

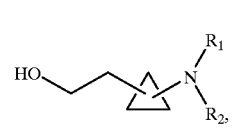

(XVIIA)

wherein $R_1$ and $R_2$ are as defined hereinbefore, which compounds of formula (XVIIA) may be subjected again, in repetitive manner, to the same series of reactions that yielded the compounds of formulae (XVI) and (XVIIA) to yield compounds of formula (XVIIB):

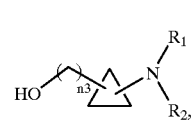

(XVIIB)

wherein $R_1$ and $R_2$ are as defined hereinbefore and $n_3$ is an integer of from 3 to 6 inclusive, the totality of the compounds of formulae (XVIIA) and (XVIIB) forming the compounds of formula (XVIII):

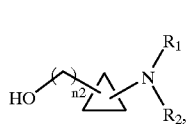

(XVIII)

wherein $R_1$ and $R_2$ are as defined hereinbefore and $n_2$ is an integer of from 2 to 6 inclusive, which compounds of formula (XVIII) are:
either reacted with a compound of formula $Y-L_1$ as described hereinbefore to yield compounds of formula (I/g), a particular case of the compounds of formula (I):

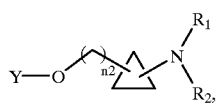

(I/g)

wherein Y, $n_2$, $R_1$ and $R_2$ are as defined hereinbefore,
or reacted with $SOCl_2$ and then treated with a compound of formula (X) as described hereinbefore to yield compounds of formula (I/h), a particular case of the compounds of formula (I),

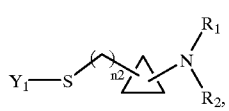

(I/h)

wherein $Y_1$, $n_2$, $R_1$ and $R_2$ are as defined hereinbefore,
or subjected to the action of an oxidising agent, the aldehyde intermediate obtained then being reacted with a hydroxylamine of formula (XII) as described hereinbefore and wherein $Y_2$ specifically represents a hydrogen atom and then, if desired, the compounds obtained are subjected to the action of a compound of formula (XIV) as described hereinbefore to yield compounds of formula (I/i), a particular case of the compounds of formula (I):

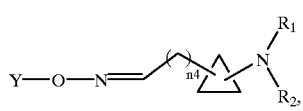

(I/i)

wherein $R_1$, $R_2$ and Y are as defined for formula (I) and $n_4$ represents an integer having a value of $(n_2-1)$ wherein $n_2$ is as defined hereinbefore,
or treated, after the action of an oxidising agent, under Wittig reaction conditions and then treated under conventional reduction conditions of organic synthesis to yield compounds of formula (I/j), a particular case of the compounds of formula (I):

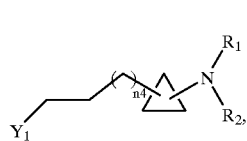

(I/j)

wherein $Y_1$, $n_4$, $R_1$ and $R_2$ are as described hereinbefore,
or reacted in the presence of $Me_3Al$ in a non-polar solvent with a compound of formula (XIX):

$HNR_1R_2$  (XIX), wherein $R_1$ and $R_2$ are as defined for formula (I), to yield compounds of formula (XX):

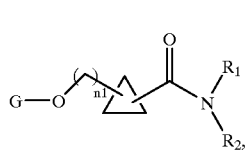

(XX)

wherein $n_1$, G, $R_1$ and $R_2$ are as defined hereinbefore,
which compounds of formula (XX) are subjected to the action of a reducing agent conventionally used in organic synthesis, to yield the compounds of formula (XXI):

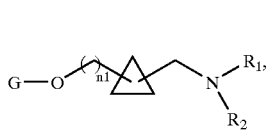

(XXI)

wherein G, $n_1$, $R_1$ and $R_2$ are as defined hereinbefore,
which compounds of formula (XXI) may be subjected to the totality of reactions to which the compounds of formula (VII) are subjected, to yield compounds of formula (I/k), a particular case of the compounds of formula (I):

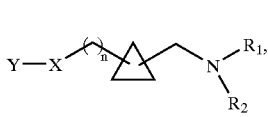

(I/k)

wherein X, Y, n, $R_1$ and $R_2$ are as defined for formula (I),
or reacted with thionyl chloride, when R represents a hydrogen atom, and then placed in the presence of diazomethane in an aqueous medium to yield compounds of formula (XXII):

(XXII)

wherein $n_1$ and G are as defined hereinbefore, which compounds of formula (XXII) may again be subjected several times to the same reaction series to yield compounds of formula (XXIII):

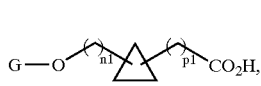
(XXIII)

wherein $n_1$ and G are as defined hereinbefore and $p_1$ represents an integer of from 2 to 6 inclusive, which compounds of formula (XXIII) are reacted with diphenylphosphoryl azide, hydrolysed and then treated with a compound of formula (VIA) as described hereinbefore to yield compounds of formula (XXIV):

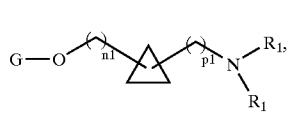
(XXIV)

wherein $R_1$ is as defined for formula (I) and G, $n_1$ and $p_1$ are as defined hereinbefore, which compounds of formula (XXIV) may be subjected to the totality of reactions to which the compounds of formula (VII) are subjected, to yield compounds of formula (I/l), a particular case of the compounds of formula (I):

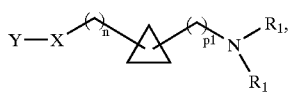
(I/l)

wherein X, Y, $R_1$ and n are as defined for formula (I) and $p_1$ is as defined hereinbefore, the totality of compounds of formulae (I/a) to (I/l) constituting the totality of the compounds of the invention, which are purified, where appropriate, according to a conventional purification technique, which may be separated into their different isomers according to a conventional separation technique, and which are converted, where appropriate, into addition salts thereof with a pharmaceutically acceptable acid or base.

We will note that in the case of compounds of formula (XI), the aldehyde is unstable when each $R_1$ and $R_2$ represents a methyl group.

According to an embodiment of the preparation process, certain compounds of the invention of formula (IA) may be obtained starting from compounds of formula ($a_1$):

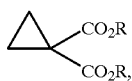
($a_1$)

wherein R represents a linear or branched ($C_1$–$C_6$)alkyl group, one of the ester functions of which compounds of formula ($a_1$) is hydrolysed, which compounds are then subjected to the action of diphenylphosphoryl azide and methanol or tert-butanol, in a polar and aprotic medium, to yield compounds of formula ($b_1$):

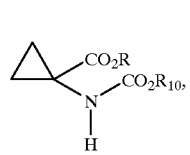
($b_1$)

wherein R is as defined hereinbefore, and $R_{10}$ represents a methyl group or a tert-butyl group, the carbamate function of which compounds of formula ($b_1$) is substituted by the action of a compound of formula ($c_1$):

$$R_1—Hal \qquad (c_1),$$

wherein $R_1$ is as defined for formula (I) and Hal represents a halogen atom, to yield compounds of formula ($d_1$):

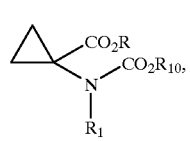
($d_1$)

wherein R, $R_1$ and $R_{10}$ are as defined hereinbefore, which compounds of formula ($d_1$) are reduced to yield compounds of formula ($e_1$) in the case where $R_{10}$ represents a methyl group, or to yield compounds of formula ($e_2$) in the case where $R_{10}$ represents a tert-butyl group;

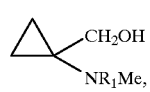
($e_1$)

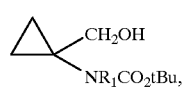
($e_2$)

wherein $R_1$ is as defined hereinbefore, which compounds of formula ($e_2$) wherein the carbamate group are deprotected under conventional conditions of organic synthesis to yield compounds of formula ($e_3$):

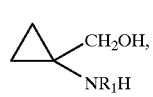
($e_3$)

wherein $R_1$ is as defined hereinbefore, which compounds of formulae ($e_1$) and ($e_3$) may be subjected to any of the reactions to which the compounds of formula (VII) are subjected in the general procedure for the formation of compounds of formula (I), to yield compounds of formula (I/m), a particular case of the compounds of formula (I):

wherein $R_1$, n, X and Y are as defined for formula (I), and $R_{20}$ represents a methyl group or a tert-butyl group, according as the compound used is a compound of formula ($e_1$) or ($e_3$).

The compounds of formulae (II), (VIA), (VIB), (VIII), (X), (XII), (XIV), (XVIII), ($a_1$) and ($c_1$) are either commercial products or are obtained according to conventional methods of organic synthesis well known to the person skilled in the art.

1,2-Disubstituted compounds of formula (II) may especially be obtained starting from hydroxyallyl or hydroxyvinyl compounds wherein the hydroxy function is protected by a conventional protecting group of organic synthesis. These compounds of formula (II/a):

wherein G is a protecting group and ni represents 0 or 1, are reacted, in the presence of rhodium tetraacetate, with a compound of formula $N_2CH_2CO_2R$, wherein R represents a linear or branched ($C_1$–$C_6$)alkyl group, to yield compounds of formula (II) as expected:

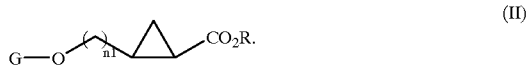

With respect to the conventional methods for protecting and deprotecting hydroxy or amino functions (groups G and $G_2$ defined in the general procedure for obtaining compounds of formula (I)), the person skilled in the art will easily refer to the book of T. W. Greene, "Protective Groups in Organic Synthesis", Willey-Interscience, New York, 1981.

Generally, isomers of the compounds of the invention are understood to be optical isomers such as enantiomers and diastereoisomers. More especially, pure enantiomeric forms of the compounds of the invention may be separated by starting from mixtures of enantiomers which are reacted with a racemate-separating agent that can be released, the said agent being itself in the form a pure enantiomer, which allows the corresponding diastereoisomers to be obtained. The diastereoisomers are then separated according to the separation techniques well known to the person skilled in the art, such as crystallisation or chromatography, and the separating agent is then removed using conventional techniques of organic synthesis, resulting in a pure enantiomer being obtained.

The compounds of the invention that are present in the form of a mixture of diastereoisomers are isolated in a pure form by using conventional separation techniques such as chromatography.

In certain particular cases, the process for the preparation of compounds of the invention may result in the predominant formation of one enantiomer or diastereoisomer over the other.

By virtue of their pharmacological properties as nicotinic ligands, and their selectivity for the receptor sub-type α4β2, the compounds of the present invention are of use in the treatment of deficiencies of memory associated with cerebral ageing and neurodegenerative diseases such as Alzheimer's disease, Parkinson's disease, Pick's disease, Korsakoff's disease and frontal lobe and subcortical dementias, and also for the treatment of mood disorders, Tourette's syndrome, attention-deficit hyperactivity syndrome, tobacco withdrawal and pain.

The present invention relates also to pharmaceutical compositions comprising as active ingredient at least one compound of formula (I), an isomer thereof, or an addition salt thereof with a pharmaceutically acceptable acid or base, alone or in combination with one or more pharmaceutically acceptable, inert, non-toxic excipients or carriers.

Among the pharmaceutical compositions according to the invention, there may be mentioned more especially those that are suitable for oral, parenteral (intravenous, intramuscular or subcutaneous), per- or trans-cutaneous, intravaginal, rectal, nasal, perlingual, buccal, ocular or respiratory administration.

Pharmaceutical compositions according to the invention for parenteral injections especially include aqueous and non-aqueous sterile solutions, dispersions, suspensions and emulsions, and also sterile powders for reconstituting injectable solutions or dispersions.

Pharmaceutical compositions according to the invention for oral administration in solid form especially include tablets or dragees, sublingual tablets, sachets, gelatin capsules and granules and, for oral, nasal, buccal or ocular administration in liquid form, especially include emulsions, solutions, suspensions, drop, syrups and aerosols.

Pharmaceutical compositions for rectal or vaginal administration are preferably suppositories, and those for per- or trans-cutaneous administration especially include powders, aerosols, creams, ointments, gels and patches.

The pharmaceutical compositions mentioned hereinbefore illustrate the invention but do not limit it in any way.

Among the pharmaceutically acceptable, inert, non-toxic excipients or carriers there may be mentioned, by way of non-limiting example, diluents, solvents, preservatives, wetting agents, emulsifiers, dispersing agents, binders, swelling agents, disintegrating agents, retardants, lubricants, absorbents, suspending agents, colourants, aromatising agents etc.

The useful dosage varies according to the age and weight of the patient, the administration route, the pharmaceutical composition used, the nature and severity of the disorder and the administration of any associated treatments. The dosage ranges from 1 mg to 500 mg per day in one or more administrations.

The Examples that follow illustrate the invention but do not limit it in any way.

The starting materials used are products that are known or that are prepared according to known operating procedures. The various Preparations yield synthesis intermediates that are useful in preparation of the compounds of the invention.

The structures of the compounds described in the Examples and Preparations were determined according to the usual spectrophotometric techniques (infrared, nuclear magnetic resonance, mass spectrometry, . . . ).

The melting points were determined using either a Kofler hot-plate or a hot-plate under a microscope. When the compound is in the form of a salt, the melting point given and the elemental microanalysis refer to the salt form of the compound.

Preparation A: (±)-cis-2-(Dimethylamino)cyclopropanol hydrochloride

Step 1: 2-(Vinyloxy)tetrahydro-2H-pyran

A mixture of 1.52 mol of 2-(2-chloroethoxy)-tetrahydro-2H-pyran, 93 g of sodium hydroxide reduced to a powder and 25 g of tetrabutylammonium monosulphate is stirred for 1 hour and then distilled at 50° C. and 20 torr. The distillate is then dried over sodium sulphate, allowing the expected product to be isolated.

Step 2: Ethyl 2-(tetrahydro-2H-pyran-2-yloxy) cyclopropanecarboxylate

To a solution of 0.75 mol of the compound obtained in Step 1 in 200 ml of ether there are added 1.5 g of rhodium acetate and then, over 6 hours, a solution of 93 g of ethyl diazoacetate in 50 ml of ether. After stirring at ambient temperature for 16 hours, the reaction mixture is filtered and is then distilled at 50–90° C. and 0.5 torr. The residue obtained is redistilled at 80–84° C. and 0.2 torr, allowing the expected product to be isolated.

Step 3: 2-(Tetrahydro-2H-pyran-2-yloxy) cyclopropanecarboxamide

In an autoclave, a solution of 0.25 mol of the compound obtained in Step 2, 2 g of sodium cyanide, 300 ml of a 2N solution of ammonia in methanol and 80 ml of liquid ammonia is heated at 65° C. for 5 days and is then concentrated to dryness. The residue is taken up in a mixture of dichloromethane/saturated potassium carbonate solution, filtered over Celite and then treated in conventional manner. After evaporating under reduced pressure, the residue is triturated in petroleum ether, filtered, rinsed and dried, allowing the expected product to be isolated.

Step 4: 2-(Tetrahydro-2H-pyran-2-yloxy) cyclopropylamine

To a cooled solution of 2.2 mol of sodium hydroxide in 800 ml of water there are added 33 g of chlorine and then 52 g of the compound obtained in Step 3. After returning to ambient temperature, the reaction mixture is heated at 65° C. for 16 hours, then cooled to 20° C. and saturated with potassium carbonate. After extracting with ether, the combined organic phases are dried and then concentrated under reduced pressure, allowing the expected product to be isolated.

Step 5: tert-Butyl 2-(tetrahydro-2H-pyran-2-yloxy) cyclopropylcarbamate 0.65 mol of triethylamine is added to a solution of 0.25 mol of the compound obtained in Step 4 in 300 ml of dichloromethane. The mixture is cooled to 0° C. and 0.3 mol of di-tert-butyl dicarbonate in 250 ml of dichloromethane is added over one hour. After returning to ambient temperature, the reaction mixture is stirred for 20 hours and then 200 ml of a saturated sodium carbonate solution are added. After separation, the organic phases are treated in customary manner and then concentrated under reduced pressure. Chromatography of the residue over silica gel (dichloromethane/ethyl acetate: 95/5) allows the expected product to be isolated in the form of a diastereoisomeric mixture.

Step 6: cis-tert-Butyl N-methyl-[2-(tetrahydro-2H-pyran-2-yloxy)cyclopropyl]-carbamate and trans-tert-butyl N-methyl-[2-tetrahydro-2H-pyran-2-yloxy)cyclopropyl] carbamate 26 g of the compound obtained in Step 5 in 20 ml of dimethylformamide are added to a solution, cooled to 0° C., of 4.4 g of sodium hydride in 250 ml of dimethylformamide. After returning to ambient temperature, the mixture is stirred for 2 hours and then 15.6 g of methyl iodide are added over 15 minutes. After stirring for 16 hours, the reaction mixture is concentrated and taken up in a mixture of ether/saturated sodium carbonate solution. The organic phases are then treated in customary manner and subsequently concentrated. Chromatography over silica gel (cyclohexane/tetrahydrofuran) allows the trans isomer and then the cis isomer of the expected product to be isolated.

Step 7: cis-N,N-Dimethyl-2-(tetrahydro-2H-pyran-2-yloxy)cyclopropanamine 46 ml of Red-Al®, 65% in toluene, are added to a solution, cooled to 0° C., of 7.5 g of the cis isomer obtained in the previous Step in 75 ml of tetrahydrofuran. The reaction mixture is stirred at 0° C. for 2 hours and at ambient temperature for 16 hours and is then cooled to 0° C. and hydrolysed with 100 ml of distilled water. After extracting with ether, the combined organic phases are treated in customary manner and then concentrated. Chromatography of the residue over silica gel (dichloromethane/tetrahydrofuran: 90/10) allows the expected product to be isolated.

Step 8: (±)-cis-2-(Dimethylamino)cyclopropanol hydrochloride 6 ml of a 4N solution of hydrochloric acid in dioxane are added, under an inert atmosphere, to 1.8 g of the compound obtained in Step 7 in 30 ml of ether. After 16 hours at ambient temperature, the mixture is filtered, rinsed with ether and then dried under reduced pressure, allowing the expected product to be isolated.

Melting point: 160–162° C.

Preparation B: (±)-trans-2-(Dimethylamino)cyclopropanol hydrochloride

Step 1: trans-N,N-Dimethyl-2-(tetrahydro-2-pyran-2-yloxy)-cyclopropanamine

The product is obtained according to the procedure of Step 7 of Preparation A using as substrate the trans isomer obtained in Step 6 of Preparation A.

Step 2: (±)-trans-2-(Dimethylamino)cyclopropanol hydrochloride

The product is obtained according to the procedure of Step 8 of Preparation A using as substrate the compound obtained in Example 1. The product recrystallises from acetonitrile.

Melting point: 118–120° C.

Preparation C: (±)-trans-Methyl 2-[(benzyloxy)methyl] cyclopropyl (methyl)carbamate Step 1: Ethyl 2-[(benzyloxy)methyl] cyclopropanecarboxylate 31.2 g of ethyl diazoacetate are added to a solution of 0.3 mol of allyl benzyl ether in 150 ml of ether with the aid of a push-syringe. After stirring for 16 hours, 31.2 g of ethyl diazoacetate are added again. After 24 hours the mixture is filtered. The organic phase is washed with saturated NaHCO$_3$ solution and then treated in customary manner. Chromatography over silica gel (dichloromethane) allows the expected product to be obtained.

Step 2: 2-[(Benzyloxy)methyl]cyclopropanecarboxylic acid

A solution of 0.23 mol of the compound obtained in Step 1 in 500 ml of ethanol, 230 ml of 1N sodium hydroxide solution and 5 ml of dimethyl sulphoxide is heated at reflux for 2 hours and is then concentrated. The residue is taken up in a mixture of water/ether. After conventional treatment, the combined organic phases are concentrated. Chromatography of the residue over silica gel (dichloromethane/tetrahydrofuran: 97/3) allows a cis/trans mixture of the products obtained to be isolated, some of the fractions of which have a preponderance of the cis isomer and some a preponderance of the trans isomer.

Step 3: (±)trans-Methyl 2-[(benzyloxy)methyl] cyclopropylcarbamate 14.7 g of diphenylphosphoryl azide are added to 11 g of the trans isomer of the product obtained in Step 2 in 100 ml of toluene, and 5.4 g of triethylamine. The mixture is heated at 80° C. for 2 hours 30 minutes, and then 2.6 g of methanol are added. After stirring at 80° C. for 16 hours, the reaction mixture is cooled, washed with saturated NaHCO₃ solution, dried and then concentrated. Chromatography of the residue over silica gel (dichloromethane) allows the expected product to be isolated in a trans/cis diastereoisomeric ratio of: 94/6.

Step 4: (±)-trans-Methyl 2-[(benzyloxy)methyl] cyclopropyl(methyl)carbamate 2.1 g of sodium hydride are added, in fractions, to a solution, cooled to 0° C., of 10.2 g of the compound obtained in Step 3 in 150 ml of dimethylformamide. After 30 minutes at 0° C., and then 24 hours at ambient temperature, 7.24 g of methyl iodide are added and stirring is carried out for 72 hours. After evaporating off the solvent, the residue is taken up in ether and washed with saturated NaHCO₃ solution and then with 10% lithium chloride solution. After customary treatment, chromatography of the residue over silica gel (dichloromethane) allows the expected product to be isolated.

Preparation D: (±)-cis-Methyl 2-[(benzyloxy)methyl] cyclopropyl-(methyl)carbamate Step 1: (±)-cis-Methyl 2-[(benzyloxy)methyl] cyclopropylcarbamate The product is obtained according to the procedure of Step 3 of Preparation C using as substrate the cis isomer obtained in Step 2 of Preparation C. The product is isolated in a cis/trans diastereoisomeric ratio of: 77/23.

Step 2: (±)-cis-Methyl 2-[(benzyloxy)methyl]cyclopropyl (methyl)carbamate

The product is obtained according to the procedure of Step 4 of Preparation C using as substrate the product obtained in Step 1.

Preparation E: trans-2-[(Dimethylamino)methyl] cyclopropanol hydrochloride

Step 1: N,N-Dimethyl-2-(tetrahydro-2H-pyran-2-yloxy) cyclopropane-carboxamide 6.1 g of dimethylamine are added, at −15° C., to 70 ml of a 2M solution of trimethyl-aluminium in toluene, and 250 ml of toluene. After 20 minutes, the mixture is brought to ambient temperature and then, after 1 hour 30 minutes, 26.3 g of the compound obtained in Step 2 of Preparation A in 75 ml of toluene are added. The reaction mixture is then heated at 85° C. for 16 hours and is then cooled in an ice bath; 270 ml of 0.5N hydrochloric acid solution are added and the mixture is filtered and separated. The combined organic phases are treated in customary manner and then concentrated under reduced pressure, allowing the expected product to be obtained in a trans/cis diastereoisomeric ratio of 80/20.

Step 2: trans-N,N-Dimethyl-N-{[2-(tetrahydro-2H-pyran-2-yloxy)-cyclopropyl]methyl}amine 14 g of the compound obtained in Step 1 in 50 ml of ether are slowly added to a suspension of 3.1 g of AlLiH₄ in 120 ml of ether. After 16 hours at reflux, the reaction mixture is cooled to 0° C., hydrolysed, filtered and then concentrated under reduced pressure. Chromatography of the residue over silica gel (dichloromethane/methanol: 90/10) allows the expected product to be isolated in a trans/cis diastereoisomeric ratio of 99/1.

Step 3: trans-2-[(Dimethylamino)methyl]cyclopropanol hydrochloride

The product is obtained according to the procedure of Step 8 of Preparation A using as substrate the compound obtained in Step 2 and adding ethanol to the reaction mixture.

Melting point: 93–96° C.

Preparation F: [1-(Dimethylamino)cyclopropyl]methanol

Step 1: 1-(Methoxycarbonyl)cyclopropanecarboxylic acid 1.45 liters of 1N sodium hydroxide solution are added to a solution, cooled to 5° C., of 1.45 ml of methyl 1,1-cyclopropanedicarboxylate in 2.5 liters of methanol. After stirring for 4 days at ambient temperature, the mixture is three-quarters concentrated, extracted with ether and then treated in customary manner, allowing the expected product to be isolated.

Step 2: Methyl 1-[(methoxycarbonyl)amino] cyclopropanecarboxylate 300 g of diphenylphosphoryl azide are added to a solution, heated to 80° C., of 1.09 mol of the compound obtained in Step 1 in 1.09 liters of toluene and 153 ml of triethylamine. The reaction is markedly exothermic. When all evolution of gas has ceased, the reaction mixture is cooled to 50° C., 66.3 ml of methanol are added, and the mixture is again heated at 70° C. for 2 hours. After cooling and conventional treatment, chromatography over silica gel (dichloromethane/methanol: 97/3) allows the expected product to be isolated.

Step 3: Methyl 1-[(methoxycarbonyl)(methyl)amino] cyclopropane-carboxylate 24.7 g of sodium hydride are added, in fractions, to a solution, cooled to 5° C., of 99.7 g of the compound obtained in Step 2 in 1.7 liters of anhydrous dimethylformamide. After 15 minutes at 5° C. and then 3 hours at ambient temperature, 38.2 ml of methyl iodide are added dropwise. After reacting for 20 hours, the mixture is evaporated. The residue is taken up in ether and then treated in conventional manner. Chromatography over silica gel (dichloromethane) allows the expected product to be isolated.

Step 4: [1-(Dimethylamino)cyclopropyl]methanol 44 g of the compound obtained in Step 3 dissolved in 350 ml of tetrahydrofuran are added, over 30 minutes, to a solution of 44 g of LiAlH₄ in 1.05 liters of tetrahydrofuran. After refluxing for 20 hours, the mixture is cooled to 5° C., and 44 ml of water, 44 ml of 4N sodium hydroxide solution and then 132 ml of water are added. Filtration, followed by concentration under reduced pressure, allows the expected product to be isolated.

Melting point: <50° C.

Preparation G: 1-[(Dimethylamino)methyl]cyclopropanol hydrochloride

Step 1: 1-Hydroxy-N,N-dimethylcyclopropanecarboxamide 17.1 ml of trimethylsilyl chloride are added dropwise to a solution of 6 g of 1-hydroxy-cyclopropanecarboxylic acid in 120 ml of dichloromethane and 10.5 ml of pyridine. After stirring for 4 hours at ambient temperature, the mixture is cooled to 0° C., and 10 drops of dimethylformamide and then 5.4 ml of oxalyl chloride are added. The reaction mixture is stirred at 0° C. for 1 hour and at ambient temperature for 1 hour; a solution of 2.4 g of dimethylamine in 10 ml of pyridine is then added. Stirring is continued for 20 hours and then, after cooling to 0° C., 14 g of citric acid in 120 ml of methanol are added. After returning to ambient temperature for one hour, the reaction mixture is washed with 1N hydrochloric acid solution and then with NaHCO₃-saturated solution and then NaCl-saturated solution. The organic phase is treated in conventional manner and chromatography over silica gel (dichloromethane/tetrahydrofuran: 90/10) allows the expected product to be isolated.

Step 2: 1-[(Dimethylamino)methyl]cyclopropanol hydrochloride 1.5 g of the compound obtained in Step 1 in 20 ml of ether are added slowly to a solution of 0.9 g of AlLiH$_4$ in 30 ml of ether. After refluxing for 5 hours, the reaction mixture is cooled and hydrolysed with ice. The aqueous phase is separated off, saturated with potassium carbonate and extracted with dichloromethane. The organic phases are dried and then concentrated under reduced pressure. The residue is taken up in 25 ml of ether and 2 ml of a 4N solution of hydrochloric acid in dioxane. The precipitate is filtered off, allowing the expected product to be isolated.

Preparation H: 2-[1-(D)imethylamino)cyclopropyl]ethanol hydrochloride

Step 1: 1-(Chloromethyl)N,N-dimethylcyclopropanamine hydrochloride 80 ml of ethereal HCl are added to a solution of 18.4 g of the compound of Preparation F in 240 ml of ether. The precipitate obtained is filtered off, rinsed with ether, dried and then diluted with 320 ml of toluene to which there are added, dropwise, 32 ml of thionyl chloride. After 3 hours at 60° C., the mixture is cooled to 5° C., filtered, washed with toluene and dried, allowing the expected product to be isolated.

Melting point: 198° C.

Step 2: [1-(Dimethylamino)cyclopropyl]acetonitrile 30.3 g of the compound obtained in Step 1 are added to a solution of 43 g of sodium cyanide and 3.5 g of potassium iodide in 400 ml of dimethyl sulphoxide. After stirring for 20 hours at ambient temperature, 490 ml of 10% aqueous sodium carbonate solution and then sodium chloride are added. The mixture is extracted with ether. After conventional treatment of the organic phases, chromatography over silica gel allows the expected product to be isolated.

Step 3: Methyl [1-(dimethylamino)cyclopropyl]acetate

To a solution, cooled to 5° C., of 14.5 g of the compound obtained in Step 2 in 230 ml of anhydrous methanol there are added 40 ml of 2N anhydrous methanolic HCl and then gaseous HCl until saturated. The mixture is stirred at ambient temperature for 20 hours and then evaporated. The residue is taken up in sodium carbonate solution and is extracted with dichloromethane. After conventional treatment of the organic phases, chromatography over silica gel (dichloromethane/tetrahydrofuran: 95/5) allows the expected product to be isolated.

Step 4: 2-[1-(Dimethylamino)cyclopropyl]ethanol hydrochloride 10.2 g of the compound obtained in Step 3 dissolved in 200 ml of tetrahydrofuran are slowly added to a solution of 5 g of AlLiH$_4$ in 300 ml of tetrahydrofuran. After refluxing for 2 hours, the reaction mixture is cooled to 5° C. and 10.7 ml of water, 10.7 ml of 4N sodium hydroxide and then 32.1 ml of water are added. After filtering and concentrating under reduced pressure, chromatography over silica gel (dichloromethane/methanol: 95/5) allows the expected product to be isolated, which is converted into its hydrochloride form by the action of a solution of hydrochloric acid in dioxane.

Preparation I: tert-Butyl 1-(hydroxymethyl)cyclopropyl(methyl)carbamate

Step 1: Methyl 1-[(tert-butoxycarbonyl)amino]cyclopropanecarboxylate

A solution of 80 g of 1-(methoxycarbonyl)cyclopropane carboxylic acid and 78 ml of triethylamine in 550 ml of toluene, to which 152 g of diphenylphosphoryl azide are added, is heated at 80° C. After the evolution of gas has ceased, the temperature is brought to 50° C. and 61 g of tert-butanol are added. After reacting for 7 hours at 80° C., the mixture is concentrated. The residue is taken up in ether, washed with saturated Na$_2$CO$_3$ solution, then with 1N hydrochloric acid solution and then with NaHCO$_3$ solution. After drying and evaporation of the organic phase, the residue is taken up in 300 ml of cyclohexane and then concentrated to dryness. The residue obtained is triturated in pentane, filtered and then dried, allowing the expected product to be isolated.

Step 2: Methyl 1-[(tert-butoxycarbonyl)(methyl)amino]cyclopropane-carboxylate

The product is obtained according to the procedure of Step 3 of Preparation F using as substrate the compound obtained in Step 1.

Step 3: tert-Butyl 1-(hydroxymethyl)cyclopropyl(methyl)carbamate 100 ml of a 2M solution of lithium borohydride in tetrahydrofuran is added to a solution of 23 g of the compound obtained in Step 2 in 100 ml of tetrahydrofuran. After stirring for 20 hours at ambient temperature and then refluxing for 8 hours, the reaction mixture is cooled to 0° C., hydrolysed, diluted with ether, separated, dried and concentrated. Chromatography of the residue over silica gel (dichloromethane/tetrahydrofuran: 95/5) allows the expected product to be isolated.

Preparation J: 1-(2-Chloroethyl)-N,N-dimethylcyclopropanamine

The product is obtained according to the procedure of Step 1 of Preparation H using as substrate the compound of Preparation H.

Preparation K: tert-Butyl 1-(hydroxymethyl)cyclopropylcarbamate

The product is obtained according to the procedure of Step 3 of Preparation I using as substrate the compound obtained in Step 1 of Preparation I.

Melting point: 80–82° C.

Preparation L: 3-[1-(Dimethylamino)cyclopropyl]-1-propanol

Step 1: tert-Butyl 1-formylcyclopropyl(methyl)carbamate

A solution of 8.3 g of dimethyl sulphoxide in 25 ml of dichloromethane is added, at −60° C., to a solution of 6.2 g of oxalyl chloride in 110 ml of dichloromethan. After 20 minutes, 8.9 g of the compound of Preparation I diluted in dichloromethane, and finally, after reacting for 30 minutes, 20 ml of triethylamine are added to the reaction mixture. After returning to ambient temperature, 50 ml of water are added and the mixture is subjected to customary treatment. Chromatography of the residue over silica gel (dichloromethane/tetrahydrofuran: 97/3) allows the expected product to be isolated.

Step 2: Ethyl 3-{1-[(tert-butoxycarbonyl)(methyl)amino]cyclopropyl}-2-propenoate 1.15 g of the product obtained in Step 1 and 2.01 g of (ethoxycarbonylmethylene)-triphenylphosphorane in 30 ml of dichloromethane are heated at reflux for 20 hours, concentrated under reduced pressure and then chromatographed over silica gel (dichloromethane/tetrahydrofuran: 97/3) allowing the expected product to be isolated.

Melting point: 52° C.

Step 3: Ethyl 3-{1-[(tert-Butoxycarbonyl)(methyl)amino]cyclopropyl}propanoate 8.0 g of the product obtained in Step 2 dissolved in 200 ml of ethanol are hydrogenated for 4 hours at 20° C. and 5 bar in the presence of 1.0 g of 10% palladium-on-carbon. After filtering and concentrating to dryness, chromatography over silica gel (dichloromethane/tetrahydrofuran: 97/3) allows the expected product to be isolated (liquid).

Step 4: 3-[1-(Dimethylamino)cyclopropyl]-1-propanol 8.5 g of the product obtained in Step 3 dissolved in 100 ml of tetrahydrofaran are added to 6.9 g of lithium aluminium hydride suspended in 200 ml of tetrahydrofuran. After refluxing for 16 hours, the mixture is cooled to 5° C. and hydrolysed with, in succession, 6.9 ml of water, 6.9 ml of 4N sodium hydroxide solution and then 20.7 ml of water. After customary treatment, chromatography of the residue over silica gel allows the expected product to be isolated (liquid).

Preparation M: tert-Butyl 1-(bromomethyl)cyclopropyl (methyl)carbamate 7.9 g of triphenylphosphine and then 9.9 g of tetrabromomethane are added, at 20° C., to a solution of 4 g of the compound of Preparation I in 100 ml of ether. After stirring for 24 hours, filtering and concentrating to dryness, chromatography over silica gel (dichloromethane) allows the expected product to be isolated.

Melting point: 62–64° C.

Preparation N: tert-Butyl (2E)-3-(3-pyridyl)-2-propenoate

Ethereal HCl is added to a solution of 45 g of (2E)-3-(3-pyridyl)-2-propenoic acid in 300 ml of ether until the pH is acid. The precipitate obtained is filtered off, washed with ether and dried under reduced pressure. The product is then taken up in 600 ml of thionyl chloride and heated at reflux for 2 hours, and is then concentrated under reduced pressure and taken up successively in toluene and then ether. The residue obtained is then diluted with 1 liter of tetrahydrofuran, stirred at 5° C., and 67 g of potassium tert-butanolate in 2.5 liters of tetrahydrofuran are added. After reacting for 3 hours at 5° C. and for 1 hour at 20° C., the reaction mixture is subjected to customary treatment, allowing the expected product to be obtained after evaporation under reduced pressure.

Melting point: oil

Preparation O: Triphenyl-(3-pyridylmethyl)phosphonium chloride 13.1 g of triphenyphosphine are added to a solution of 8.2 g of 3-picolyl chloride hydrochloride in 120 ml of dimethylformamide. After stirring for 5 minutes, the mixture is heated at reflux for 30 minutes in a microwave apparatus and then cooled to 5° C. The crystals obtained are filtered off, rinsed with dimethylformamide and then with ether, and dried under reduced pressure, allowing the expected product to be isolated.

Melting point: 315–318° C.

Preparation P: [1-(1-Pyrrolidinyl)cyclopropyl]methanol

Step 1: 1-(1-Pyrrolidinyl)cyclopropanecarbonitrile

A mixture containing a drop of trimethylsilyl chloride and 67.8 g of [(1-ethoxycyclopropyl)oxy]trimethylsilane in 65 ml of methanol is added to 62.6 g of pyrrolidine hydrochloride and 28.7 g of potassium cyanide dissolved in 260 ml of methanol. After stirring for 20 minutes at 20° C., and then for 20 hours at 50° C., the reaction mixture is concentrated to dryness, taken up in dichloromethane, filtered and concentrated to dryness again. The residue is chromatographed over silica gel ($CH_2Cl_2$) allowing the desired product to be isolated.

Step 2: 1-(1-Pyrrolidinyl)cyclopropanecarboxamide

For 5 hours, a stream of gaseous HCl is, at 20° C., bubbled through a mixture containing 5.2 g of the product obtained in Step 1 dissolved in 100 ml of methanol. The mixture is concentrated to dryness, taken up in 20 ml of aqueous sodium carbonate solution and 20 ml of dichloromethane. After customary treatment, chromatography over silica gel allows the expected product to be isolated.

Melting point: 62° C.

Step 3: Ethyl 1-(1-pyrrolidinyl)cyclopropanecarboxylate

A solution containing 11.4 g of triethyloxonium tetrafluoroborate and 40 ml of dichloromethane is added dropwise, at 0° C., to a suspension containing 1.54 g of the product obtained in Step 2, 10 g of disodium hydrogen phosphate and 120 ml of dichloromethane. After 20 hours at 20° C., 40 ml of 10% aqueous sodium carbonate solution are added. The mixture is separated and the aqueous phase is extracted with dichloromethane. The combined organic phases are dried over sodium sulphate and then concentrated to dryness. The residue is taken up in 1N aqueous hydrochloric acid and the resulting solution is left at 20° C. for 3 hours. The mixture is made alkaline with sodium carbonate and extracted with dichloromethane. The combined dichloromethane phases are dried over sodium sulphate and concentrated to dryness. Chromatography over silica gel (dichloromethane/tetrahydrofuran: 95/5) allows the desired product to be isolated.

Step 4: [1-(1-Pyrrolidinyl)cyclopropyl]methanol 20.5 g of the product obtained in Step 3 and 100 ml of tetrahydrofuran are poured, over 5 minutes, into a suspension containing 8.57 g of lithium aluminium hydride and 400 ml of tetrahydrofuran. The mixture is heated at reflux for 2 hours, cooled to 5° C. and hydrolysed by successive additions of 9 ml of water, 9 ml of 4N sodium hydroxide solution and then 27 ml of water. The aluminium compound is filtered off and rinsed with tetrahydroflran. The combined filtrates are concentrated to dryness, allowing the desired product to be obtained (liquid).

Preparation Q: tert-Butyl 1-(2-hydroxyethyl)cyclopropyl (methyl)carbamate

Step 1: tert-Butyl 1-(bromomethyl)cyclopropyl(methyl)carbamate 100.1 g of triphenylphosphine and then 125.5 g of tetrabromomethane are added to a solution containing 50.7 g of the product of Preparation I in 1.25 liters of ether. Stirring is carried out at 20° C. for 20 hours, the insoluble material is filtered off and concentration to dryness is carried out. The residue is chromatographed over silica gel ($CH_2Cl_2$), which allows the expected product to be isolated.

Melting point: 53° C.

Step 2: tert-Butyl 1-(cyanomethyl)cyclopropyl(methyl) carbamate

A mixture containing 26.4 g of the product of Step 1, 26 g of potassium cyanide and 2.6 g of potassium iodide in 264 ml of dimethyl sulphoxide is stirred at 70° C. for 20 hours. The mixture is cooled and 400 ml of 10% sodium carbonate in water are added. After extraction with ether and customary treatment, evaporation of the residue under reduced pressure allows the expected product to be isolated.

Step 3: Methyl [1-(methylamino)cyclopropyl]acetate 89 ml of 4N methanolic HCl are added to a solution containing 22.2 g of the product obtained in Step 2 dissolved in 450 ml of methanol. 200 g of gaseous HCl are bubbled in at a temperature lower than 40° C. The mixture is left to stand for 20 hours at ambient temperature and is then concentrated to dryness; the residue is taken up in 80 ml of 10% sodium carbonate. After customary treatment, chromatography over silica gel ($CH_2Cl_2$/ethanol: 97/3) allows the desired product to be isolated.

Step 4: Methyl {1-[(tert-butoxycarbonyl)(methyl)amino] cyclopropyl}acetate

A solution containing 17.5 g of di-tert-butyl dicarbonate and 120 ml of dichloromethane is added dropwise at 5° C. to a solution containing 9.5 g of the product obtained in Step 3 and 0.88 g of (3-dimethylamino)pyridine in 120 ml of dichloromethane. After 2 hours at 5° C., and then 2 hours at 20° C., the mixture is washed with aqueous ammonium chloride solution and then with 10% sodium hydrogen carbonate solution. After customary treatment, evaporation under reduced pressure allows the desired product to be obtained.

Step 5: tert-Butyl 1-(2-hydroxyethyl)cyclopropyl(methyl)carbamate

Over 20 minutes, 20 ml of 2M lithium borohydride in tetrahydrofuran is poured, at 20° C., into a mixture containing 4.86 g of the product obtained in Step 4 and 20 ml of tetrahydrofuran. After stirring for 20 hours at ambient temperature and then for 1 hour at reflux, the mixture is cooled to 5° C. and then hydrolysed using a mixture containing 8 ml of water and 4 ml of 10% aqueous sodium carbonate solution. The aqueous phase is extracted several times with ether. After customary treatment, chromatography of the residue over silica gel ($CH_2Cl_2$/tetrahydrofuran: 98/2) allows the expected product to be isolated (liquid).

Preparation R: 2-[1-(1-Pyrrolidinyl)cyclopropyl]ethanol

Step 1: tert-Butyl 1-(bromomethyl)cyclopropylcarbamate

The product is obtained according to the procedure of Preparation M using as substrate the product of Preparation K.

Melting point: 96° C.

Step 2: tert-Butyl 1-(cyanomethyl)cyclopropylcarbamate

The product is obtained according to the procedure of Preparation H Step 2, using as substrate the product obtained above.

Melting point: 89° C.

Step 3: Methyl [1-(amino)cyclopropyl]acetate

The product is obtained according to the procedure of Preparation H Step 3, using as substrate the product obtained above.

Step 4: Methyl [1-(2,5-dioxo-1-pyrrolidinyl)cyclopropyl]acetate

A solution containing 1.29 g of the product obtained in the previous Step and 1 g of succinic anhydride in 30 ml of toluene is heated at reflux for 1 hour, and then 2.8 ml of triethylamine are added. After 20 hours at reflux, the mixture is concentrated to dryness. The residue is then taken up in toluene and subsequently evaporated under reduced pressure. Chromatography over silica gel (dichloromethane/tetrahydrofuran: 97/3) allows the expected product to be isolated.

Step 5: 2-[1-(1-Pyrrolidinyl)cyclopropyl]ethanol

The product is obtained according to the procedure of Preparation L Step 4, using as substrate the product obtained above (liquid).

Preparation S: tert-Butyl methyl-[1-(2-oxoethyl)cyclopropyl]carbamate

The product is obtained according to the procedure of Preparation L Step 1, using as substrate the product of Preparation Q.

Melting point: 93° C.

EXAMPLE 1

(±)-cis-2-(Dimethylamino)cyclopropyl acetate hydrochloride

A solution, under an inert atmosphere, of 0.28 g of the compound of Preparation A in 4 ml of acetic acid, to which 0.22 g of acetyl chloride is added, is stirred at ambient temperature for 16 hours and is then concentrated. The residue is taken up in 10 ml of dioxane and concentrated to dryness again. The operation is repeated until crystallisation occurs. The crystals obtained are diluted in 10 ml of ether, filtered off and dried, allowing the expected product to be isolated.

Melting point: amorphous

| Elemental microanalysis: | | | | |
|---|---|---|---|---|
| | C | H | N | Cl |
| % calculated | 46.11 | 7.90 | 7.68 | 19.44 |
| % found | 46.01 | 7.70 | 7.48 | 19.63 |

EXAMPLE 2

(±)-cis-2-(Dimethylamino)cyclopropyl methylcarbamate hydrochloride

A solution of 0.4 g of the compound of Preparation A in 30 ml of acetonitrile and 0.25 g of methyl isocyanate is heated at 80° C. for 8 hours, and then evaporated. The residue is taken up in a mixture of water/ether, and saturated with potassium carbonate. The organic phase is treated in customary manner and the residue is chromatographed over silica gel (dichloromethane/methanol: 97/3). The compound obtained is converted into its hydrochloride form in customary manner. The product obtained crystallises from a mixture of 5% acetonitrile in ether.

Melting point: 105–110° C.

| Elemental microanalysis: | | | | |
|---|---|---|---|---|
| | C | H | N | Cl |
| % calculated | 41.65 | 7.89 | 13.88 | 17.56 |
| % found | 41.68 | 7.88 | 13.93 | 18.25 |

EXAMPLE 3

(±)-trans-2-(Dimethylamino)cyclopropyl acetate hydrochloride

The product is obtained according to the procedure of Example 1 using as substrate the compound of Preparation B.

Melting point: 148–150° C.

| Elemental microanalysis: | | | | |
|---|---|---|---|---|
| | C | H | N | Cl |
| % calculated | 46.80 | 7.85 | 7.80 | 19.83 |
| % found | 46.67 | 7.82 | 7.50 | 19.97 |

EXAMPLE 4

(±)-trans-2-(Dimethylamino)cyclopropyl methylcarbamate hydrochloride

The product is obtained according to the procedure of Example 2 using as substrate the compound of Preparation B.

Melting point: 158–160° C.

| Elemental microanalysis: | | | | |
|---|---|---|---|---|
| | C | H | N | Cl |
| % calculated | 42.60 | 7.81 | 14.19 | 17.96 |
| % found | 42.54 | 7.69 | 13.97 | 18.09 |

EXAMPLE 5

(±)-trans-2-[(Benzyloxy)methyl]-N,N-dimethylcyclopropanamine hydrochloride

A solution, cooled to 5° C., of 7 g of the compound of Preparation C in 140 ml of tetrahydrofuran, to which there are added 60 ml of Red-Al® 65% solution in toluene, is stirred for 2 hours at 5° C. and for 16 hours at ambient temperature and is then cooled to 0° C. and hydrolysed. The solution is then diluted with ether, filtered and separated, and the organic phase is concentrated. The residue is converted into its hydrochloride form in conventional manner, allowing the expected product to be obtained.

Melting point: 118–120° C.

| Elemental microanalysis: | | | | |
|---|---|---|---|---|
| | C | H | N | Cl |
| % calculated | 64.59 | 8.34 | 5.79 | 14.66 |
| % found | 64.14 | 8.46 | 5.78 | 14.54 |

EXAMPLE 6

(±)-cis-2-[(Benzyloxy)methyl]-N,N-dimethylcyclopropanamine hydrochloride

The product is obtained according to the procedure of Example 5 using as substrate the compound of Preparation D.

Melting point: 90–92° C.

| Elemental microanalysis: | | | | |
|---|---|---|---|---|
| | C | H | N | Cl |
| % calculated | 64.59 | 8.34 | 5.79 | 14.66 |
| % found | 64.35 | 8.07 | 5.84 | 14.84 |

EXAMPLE 7

(±)-trans-[2-(Dimethylamino)cyclopropyl]methyl acetate hydrochloride

Step 1: (±)-trans-[2-(Dimethylamino)cyclopropyl]methanol hydrochloride 1.2 g of sodium are added, in portions, to a solution of 4 g of the compound of Example 5 in 200 ml of condensed liquid ammonia. After 3 hours, 100 ml of ether and then 5 ml of ethanol are added. Stirring is carried out for 16 hours and the mixture is then concentrated and taken up in dichloromethane. The organic phase is treated in conventional manner and then evaporated. Chromatography over silica gel (dichloromethane/methanol: 90/10) allows the expected product to be isolated, which is converted into its hydrochloride form.

Melting point: 88–90° C.

Step 2: (±)-trans-[2-(Dimethylamino)cyclopropyl]methyl acetate hydrochloride

The product is obtained according to the procedure of Example 1 using as substrate the compound obtained in Step 1.

Melting point: 144–146° C.

| Elemental microanalysis: | | | | |
|---|---|---|---|---|
| | C | H | N | Cl |
| % calculated | 49.61 | 8.33 | 7.23 | 18.31 |
| % found | 49.58 | 8.34 | 7.11 | 18.09 |

EXAMPLE 8

(±)-cis-[2-(Dimethylamino)cyclopropyl]methyl acetate hydrochloride

Step 1: (±)-cis-[2-(Dimethylamino)cyclopropyl]methanol hydrochloride

The product is obtained according to the procedure of Step 1 of Example 7 using as substrate the compound of Example 6.

Melting point: 112–114° C.

Step 2: (±)-cis-[2-(Dimethylamino)cyclopropyl]methyl acetate hydrochloride

The product is obtained according to the procedure of Example 1 using as substrate the compound obtained in Step 1.

Melting point: 108–110° C.

| Elemental microanalysis: | | | | |
|---|---|---|---|---|
| | C | H | N | Cl |
| % calculated | 49.61 | 8.33 | 7.23 | 18.31 |
| % found | 49.37 | 8.34 | 7.16 | 18.24 |

EXAMPLE 9

(±)-trans-2-[(Dimethylamino)methyl]cyclopropyl acetate hydrochloride

The product is obtained according to the procedure of Example 1 using as substrate the compound of Preparation E.

Melting point: 100–105° C.

| Elemental microanalysis: | | | | |
|---|---|---|---|---|
| | C | H | N | Cl |
| % calculated | 49.61 | 8.33 | 7.23 | 18.31 |
| % found | 49.32 | 8.37 | 7.11 | 18.26 |

EXAMPLE 10

[1-(Dimethylamino)cyclopropyl]methyl acetate hydrochloride

The product is obtained according to the procedure of Example 1 using as substrate the compound of Preparation F.

Melting point: 100–102° C.

| Elemental microanalysis: | | | | |
|---|---|---|---|---|
| | C | H | N | Cl |
| % calculated | 49.61 | 8.33 | 7.23 | 18.31 |
| % found | 49.27 | 8.37 | 7.16 | 18.28 |

EXAMPLE 11

[1-(Dimethylamino)cyclopropyl]methyl dimethylcarbamate hydrochloride

To a solution, under an inert atmosphere, of 2.1 g of the compound of Preparation F in 20 ml of pyridine there are added 1.95 g of dimethylcarbamoyl chloride and then, after 48 hours at ambient temperature, the same amount of reagent. The reaction mixture is heated at reflux for 3 hours and then evaporated. The residue is taken up in dioxane and then concentrated again, taken up in ether and washed with NaHCO$_3$ solution. The organic phase is extracted with 0.1N HCl solution, and the aqueous phase is made alkaline with sodium carbonate and then extracted with ether. The organic phases are treated in conventional manner and concentrated. Chromatography of the residue over silica gel (dichloromethane/tetrahydrofuran: 90/10) allows the expected product to be isolated, which is converted into its hydrochloride form.

Melting point: 166–168° C.

| Elemental microanalysis: | | | | |
|---|---|---|---|---|
| | C | H | N | Cl |
| % calculated | 48.54 | 8.60 | 12.58 | 15.92 |
| % found | 48.55 | 8.53 | 12.22 | 15.61 |

EXAMPLE 12

1-[(Dimethylamino)methyl]cyclopropyl acetate hydrochloride

The product is obtained according to the procedure of Example 1 using as substrate the compound of Preparation G.

Melting point: 166–170° C.

| Elemental microanalysis: | | | | |
|---|---|---|---|---|
| | C | H | N | Cl |
| % calculated | 49.61 | 8.33 | 7.23 | 18.31 |
| % found | 49.52 | 8.46 | 7.21 | 18.88 |

EXAMPLE 13

2-[1-(Dimethylamino)cyclopropyl]ethyl acetate hydrochloride

The product is obtained according to the procedure of Example 1 using as substrate the compound of Preparation H.

Melting point: 79–81° C.

| Elemental microanalysis: | | | | |
|---|---|---|---|---|
| | C | H | N | Cl |
| % calculated | 51.16 | 8.78 | 6.63 | 16.78 |
| % found | 51.05 | 8.60 | 6.90 | 16.94 |

EXAMPLE 14

2-[1-(Dimethylamino)cyclopropyl]ethyl dimethylcarbamate fumarate

A solution, at 5° C., of 1.3 g of the compound of Preparation H in 25 ml of tetrahydrofuran, to which is added 0.4 g of sodium hydride, is stirred for 10 minutes at 5° C., for 1 hour at ambient temperature and then for 2 hours at 40° C. and is finally brought to 5° C. 1.2 g of dimethylcarbamoyl chloride are then added slowly and the reaction mixture is stirred for 1 hour at 5° C., for 1 hour at ambient temperature and then for 7 hours at 40° C. and is finally concentrated under reduced pressure. The residue is taken up in dichloromethane, washed with saturated sodium chloride solution, dried and concentrated. Chromatography over silica gel (ethyl acetate) allows the expected product to be isolated, which is converted into its fumarate form in conventional manner.

Melting point: 148–149° C.

| Elemental microanalysis: | | | |
|---|---|---|---|
| | C | H | N |
| % calculated | 53.15 | 7.65 | 8.86 |
| % found | 52.71 | 7.52 | 8.56 |

EXAMPLE 15

2-[1-(Dimethylamino)cyclopropyl]ethyl methylcarbamate fumarate 0.63 g of methyl isocyanate is added to a solution, cooled to 5° C., of 1.3 g of the compound of Preparation H in 26 ml of ether, and the mixture is then heated at reflux for 4 hours. The additions of methyl isocyanate are repeated three times, alternating with periods of refluxing of 4 hours. After the reaction has ceased, the mixture is concentrated under reduced pressure. Chromatography of the residue over silica gel (dichloromethane/methanol: 95/5) allows the expected product to be isolated, which is converted into its fumarate form according to a conventional procedure.

Melting point: 118–119° C.

| Elemental microanalysis: | | | |
|---|---|---|---|
| | C | H | N |
| % calculated | 51.65 | 7.33 | 9.27 |
| % found | 51.67 | 7.38 | 9.08 |

EXAMPLE 16

[1-(Dimethylamino)cyclopropyl]methyl nicotinate hydrochloride

A solution of 0.9 g of nicotinic acid chloride hydrochloride, 0.76 g of the compound of Preparation F and 0.06 g of 4-dimethylaminopyridine in 15 ml of pyridine is heated at 80° C. for 5 hours and is then concentrated under reduced pressure. The residue is taken up in a mixture of ether and saturated NaHCO$_3$ solution. The organic phase is treated in conventional manner and is then concentrated. Chromatography over silica gel (dichloromethane/methanol: 97/3) allows the product to be isolated, which is converted into its hydrochloride form in conventional manner.

Melting point: >130° C.

| Elemental microanalysis: | | | | |
|---|---|---|---|---|
| | C | H | N | Cl |
| % calculated | 45.01 | 6.61 | 8.75 | 22.14 |
| % found | 45.06 | 6.70 | 8.61 | 21.03 |

EXAMPLE 17

N,N-Dimethyl-1-[(3-pyridylmethoxy)methyl] cyclopropanamine hydrochloride 1.32 g of sodium hydride are added to a solution of 3.4 g of the compound of Preparation F in 55 ml of dimethylformamide. The reaction mixture is held at 45° C. for 1 hour 30 minutes and is then brought to ambient temperature before being cooled to 0° C.; 0.036 mol of 3-picolyl chloride is added. The reaction mixture is stirred for 16 hours at ambient temperature followed by 5 hours at 50° C., and is then concentrated under reduced pressure. The residue is taken up in saturated sodium carbonate solution and is then extracted with ethyl acetate. The organic phase is treated in conventional manner and evaporated. Chromatography of the residue over silica gel (dichloromethane/methanol: 97.5/2.5) allows the expected product to be isolated, which is converted into its hydrochloride in conventional manner.

Melting point: 205–210° C.

| Elemental microanalysis: | | | | |
|---|---|---|---|---|
| | C | H | N | Cl |
| % calculated | 51.62 | 7.22 | 10.03 | 25.40 |
| % found | 51.72 | 7.22 | 9.78 | 25.46 |

EXAMPLE 18

N-Methyl-1-[(3-pyridyloxy)methyl] cyclopropanamine hydrochloride

Step 1: tert-Butyl N-methyl-{1-[(3-pyridyloxy)methyl] cyclopropyl}carbamate 4.7 ml of diethyl azodicarboxylate are added to a solution, cooled to 0° C., of 7.9 g of triphenylphosphine in 80 ml of tetrahydrofuran. After 45 minutes, the reaction mixture is brought to ambient temperature and 2.9 g of 3-hydroxypyridine and 4 g of the compound of Preparation I suspended in 40 ml of tetrahydrofuran are added. After stirring for 24 hours, the mixture is concentrated under reduced pressure and then 100 ml of 1N hydrochloric acid are added. The aqueous phase is extracted with ethyl acetate, made alkaline by the addition of solid potassium carbonate and re-extracted with ether. The combined organic phases are treated in customary manner and then evaporated. Chromatography over silica gel (dichloromethane/tetrahydrofuran: 97/3) allows the expected product to be isolated.

Step 2: N-Methyl-1-[(3-pyridyloxy)methyl] cyclopropanamine hydrochloride

A solution containing 0.32 g of the compound obtained in Step 1 in 3 ml of dioxane and 3 ml of 4N hydrochloric acid in dioxane is stirred at ambient temperature and under an inert atmosphere, and is then diluted with ether. The liquid phase is then separated off and the residue is taken up in 25 ml of ethanol. The solution is concentrated to 2 ml and is then diluted with 20 ml of ether and stirred; the precipitate formed is filtered off, rinsed and dried, allowing the expected product to be isolated.

Melting point: 152–155° C.

| Elemental microanalysis: | | | | |
|---|---|---|---|---|
| | C | H | N | Cl |
| % calculated | 46.82 | 6.52 | 10.92 | 27.64 |
| % found | 46.83 | 6.48 | 10.68 | 27.68 |

EXAMPLE 19

N,N-Dimethyl-1-[(3-pyridyloxy)methyl] cyclopropanamine hydrochloride 1.07 g of the compound of Example 18 diluted with 1.2 ml of water are added to a solution, cooled to 0° C., of 1.38 g of formic acid, 1.12 ml of 37% formaldehyde in water and 0.15 ml of distilled water. The reaction mixture is heated at reflux for 16 hours and is then cooled to 0° C. and 10 ml of 4N sodium hydroxide solution are added. The mixture is extracted with ether. The organic phase is treated in customary manner and evaporated. The residue is taken up in ethanol, concentrated again and then diluted with 20 ml of ether and 4 ml of 4N hydrochloric acid solution in dioxane. The mixture is stirred for 20 minutes, filtered, rinsed with ether and dried, allowing the expected product to be isolated.

Melting point: 215–220° C.

EXAMPLE 20

N,N-Dimethyl-1-[2-(3-pyridyloxy)ethyl]cyclopropanamine dihydrochloride

A solution containing 0.58 g of 3-hydroxypyridine sodium salt in 5 ml of dimethyl sulphoxide and 0.46 g of the compound of Preparation J is heated at reflux for 16 hours and is then brought to ambient temperature and taken up in a mixture of ether/saturated sodium carbonate solution. After being separated off, the aqueous phase is extracted with ethyl acetate and the organic phases are then washed with 1N sodium hydroxide solution and then with 10% lithium chloride solution. After concentration, the residue is taken up in 20 ml of ether and the dihydrochloride of the expected product is obtained in conventional manner.

Melting point: 173–175° C.

| Elemental microanalysis: | | | | |
|---|---|---|---|---|
| | C | H | N | Cl |
| % calculated | 59.75 | 7.31 | 11.34 | 24.97 |
| % found | 50.76 | 7.28 | 9.72 | 24.37 |

EXAMPLE 21

4-({2-[1-(Dimethylamino)cyclopropyl]ethyl}sulphanyl)phenol hydrochloride

A solution containing 0.4 g of 90% 4-hydroxythiophenol, 0.46 g of the compound of Preparation J in 10 ml of dimethylformamide and 0.7 g of potassium carbonate is stirred for 24 hours at ambient temperature and is then diluted with ether. The mixture is acidified by the addition of 15 ml of 1N hydrochloric acid and is then separated. The organic phase is re-extracted with 15 ml of 1N hydrochloric acid and the aqueous phases are made alkaline and extracted with ethyl acetate. After drying of the acetylated phases and concentration thereof, the residue obtained corresponds to the expected product, which is converted into its hydrochloride form in conventional manner.

Melting point: 193–195° C.

EXAMPLE 22

1-[(3-Pyridyloxy)methyl]cyclopropanamine dihydrochloride

Step 1: tert-Butyl 1-[(3-pyridyloxy)methyl]cyclopropylcarbamate

The product is obtained according to the procedure of Step 1 of Example 18 using as substrate the compound of Preparation K.

Melting point: 112–114° C.

Step 2: 1-[(3-Pyridyloxy)methyl]cyclopropanamine dihydrochloride

The product is obtained according to the procedure of Example 18 Step 2 using as substrate the compound obtained in Step 1.

Melting point: 120–122° C.

EXAMPLE 23

N-Methyl-1-{[(6methyl-3-pyridyl)oxy]methyl}cyclopropanamine hydrochloride

Step 1: tert-Butyl methyl(1-{[(methyl-3-pyridyl)oxy]methyl}cyclopropyl)carbamate The product is obtained according to the procedure of Step 1 of Example 18 using as substrate the compound of Preparation I and 6-methyl-pyridin-3-ol.

Melting point: 62–64° C.

Step 2: N-Methyl-1-{[(6-methyl-3-pyridyl)oxy]methyl}cyclopropanamine hydrochloride The product is obtained according to the procedure of Example 18 Step 2 using as substrate the compound obtained in Step 1.

Melting point: 172–175° C.

EXAMPLE 24

N-Methyl-1-{[(6-chloro-3-pyridyl)oxy]methyl}cyclopropanamine hydrochloride

Step 1: tert-Butyl methyl(1-{[(6-chloro-3-pyridyl)oxy]methyl}cyclopropyl)carbamate The product is obtained according to the procedure of Step 1 of Example 18 using as substrate the compound of Preparation I and 2-chloro-5-hydroxypyridine.

Melting point: 70–72° C.

Step 2: N-Methyl-1-{[(6-chloro-3-pyridyl)oxy]methyl}cyclopropanamine hydrochloride The product is obtained according to the procedure of Example 18 Step 2 using as substrate the compound obtained in Step 1.

Melting point: 120–122° C.

EXAMPLE 25

N-{1-[(3-Fluorophenoxy)methyl]cyclopropyl}-N-methylamine hydrochloride

Step 1: tert-Butyl methyl(1-{[(methyl-3-pyridyl)oxy]methyl}cyclopropyl)carbamate The product is obtained according to the procedure of Step 1 of Example 18 using as substrate the compound of Preparation I and 3-fluorophenol.

Step 2: N-{1-[(3-Fluorophenoxy)methyl]cyclopropyl}-N-methylamine hydrochloride

The product is obtained according to the procedure of Example 18 Step 2 using as substrate the compound obtained in Step 1.

Melting point: 98–100° C.

EXAMPLE 26

3-[1-(Dimethylamino)cyclopropyl]propyl dimethylcarbamate fumarate

The product is obtained according to the procedure of Example 11 using as substrate the compound obtained in Preparation L.

Melting point: 110–111° C.

EXAMPLE 27

3-[1-(Dimethylamino)cyclopropyl]propyl methylcarbamate fumarate

The product is obtained according to the procedure of Example 15 using as substrate the compound obtained in Preparation L.

Melting point: 150–151° C.

EXAMPLE 28

N-Methyl-1-[(2-pyridylsulphanyl)methyl] cyclopropanamine dihydrochloride

Step 1 tert-Butyl methyl{1-[(2-pyridylsulphanyl)methyl] cyclopropyl}-carbamate 1.75 g of potassium carbonate are added to a solution of 1.33 g of 2-mercaptopyridine and 2.65 g of the compound of Preparation M in 25 ml of dimethylformamide. After stirring for 24 hours at 20° C., the reaction mixture is taken up in ether, filtered and concentrated. Chromatography of the residue over silica gel (dichloromethane) allows the expected product to be isolated Melting point: 62–64° C.

Step 2: N-Methyl-1-[(2-pyridylsulphanyl)methyl] cyclopropanamine dihydrochloride The product is obtained according to the procedure of Example 18 Step 2 using as substrate the compound obtained in Step 1.

Melting point: 174–178° C.

EXAMPLE 29

N-Methyl-1-[3-(3-pyridyloxy)propyl] cyclopropanamine dihydrochloride

Step 1: tert-Butyl methyl{1-[3-(3-pyridyloxy)propyl] cyclopropyl}carbamate

The product is obtained according to the procedure of Step 1 of Example 18 using as substrate the compound of Preparation L.

Step 2: N-Methyl-1-[3-(3-pyridyloxy)propyl] cyclopropanamine dihydrochloride

The product is obtained according to the procedure of Example 18 Step 2 using as substrate the compound obtained in Step 1.

Melting point: 118–120° C.

EXAMPLE 30

N-Methyl-1-[2-(3-pyridyl)ethyl]cyclopropanamine dihydrochloride

Step 1: tert-Butyl methyl{1-[(Z)-2-(3-pyridyl)ethenyl] cyclopropyl}carbamate 24.7 g of the product obtained in Preparation O are added to a mixture containing 6.5 g of potassium tert-butanolate in 100 ml of dimethyl sulphoxide. After stirring for 1 hour, 5.5 g of the product obtained in Step 1 of Preparation L in 20 ml of dimethyl sulphoxide are added. After reacting for 1 hour 30 minutes, the mixture is diluted with ether and 120 ml of water are added. The organic phases are extracted with 1N hydrochloric acid and then treated in customary manner. Chromatography of the residue over silica gel (dichloromethane/tetrahydrofuran: 97/3) allows the expected product to be isolated.

Step 2: tert-Butyl methyl{1-[2-(3-pyridyl)ethyl] cyclopropyl}carbamate 5.1 g of the product obtained in Step 1 dissolved in 120 ml of methanol are hydrogenated in the presence of 1 g of 10% palladium-on-carbon (20° C., 1 bar, 3 hours). The catalyst is filtered off and rinsed with methanol; concentrating to dryness and drying at 45° C. and 0.5 torr allows the desired product to be obtained.

Step 3: N-Methyl-1-[2-(3-pyridyl)ethyl] cyclopropanamine dihydrochloride 20 ml of 4N hydrochloric acid in dioxane are added to a mixture containing 4.4 g of the product obtained in Step 2 in 20 ml of dioxane. Stirring is carried out for 4 hours at 20° C. and then 20 ml of ether are added. Crystallisation is observed. The crystals are filtered off, washed with ether and dried at 50° C. and 0.5 torr, allowing the expected product to be obtained.

Melting point: 202–205° C.

EXAMPLE 31

N-Methyl-1-[(Z)-2-(3-pyridyl)ethenyl] cyclopropanamine fumarate 12 ml of 4N hydrochloric acid in dioxane are added to a mixture containing 2.3 g of the product obtained in Step 1 of Example 30 dissolved in 12 ml of dioxane; stirring is carried out for 4 hours at 20° C., 30 ml of ether are then added and stirring is continued for 16 hours at 20° C. A precipitate is formed and the supernatant phase is separated off. The residue is taken up in aqueous sodium carbonate solution and is then extracted several times with ether. The combined ether phases are dried over sodium sulphate and concentrated to dryness. The residue is dissolved in ethanol and 1.2 g of fumaric acid dissolved in ethanol are added, allowing the expected product to be isolated once the crystals formed have been filtered off and rinsed with ether.

Melting point 116–118° C.

EXAMPLE 32

[1-(1-Pyrrolidinyl)cyclopropyl]methyl dimethylcarbamate fumarate 0.62 g of sodium hydride is added to a solution of 1.98 g of the product of Preparation P in 40 ml of tetrahydrofuran. The mixture is stirred for 20 minutes at 5° C., for 1 hour at 20° C. and for 2 hours at 40° C., and is then cooled to 5° C. and 1.8 g of dimethylcarbamoyl chloride dissolved in 10 ml of tetrahydrofuran are added. After 30 minutes, the reaction mixture is brought to ambient temperature for 20 hours and then evaporated. The residue is taken up in dichloromethane and treated in customary manner. Chromatography over silica gel (dichloromethane/methanol: 97/3) allows the desired product to be isolated, which is converted into fumarate by the addition of 0.95 g of fumaric acid.

Melting point: 123–124° C.

EXAMPLE 33

N,N-Dimethyl-1-[2-(3-pyridyl)ethyl] cyclopropanamine hydrochloride 1.5 g of the compound of Example 30 are dissolved in 10% aqueous sodium carbonate solution; the mixture is then extracted with ether, dried over sodium sulphate and concentrated to dryness. 1.17 ml of formol and 1.43 g of formic acid at 5° C. are then added to the residue obtained, followed by 0.15 ml of water. The mixture is heated at reflux for 5 hours, cooled to 50° C. and then made alkaline by the addition of 4N sodium hydroxide solution. Extraction with ether, followed by evaporation of the aqueous phase allows a residue to be obtained which is taken up in a mixture of 20 ml of ether and 3 ml of dioxane/4N hydrochloric acid. The mixture obtained is diluted with 50 ml of ether and stirred for 20 hours, and is then filtered and dried, allowing the expected product to be isolated.

Melting point: 200–203° C.

EXAMPLE 34

3-{[1-(1-Pyrrolidinyl)cyclopropyl]methoxy}pyridine fumarate 15.2 g of diisopropyl azodicarboxylate are introduced dropwise, at −15° C., into a mixture containing 19.7 g of triphenylphosphine and 300 ml of tetrahydrofuran and the mixture is then cooled to −20° C.; there are then added, in small fractions, 4.95 g of 3-hydroxypyridine dissolved in 25 ml of tetrahydrofuran, and then 7.06 g of the compound of Preparation P dissolved in 25 ml of tetrahydrofuran. After 20 hours at −20° C., the mixture is concentrated to dryness and then cyclohexane is added to the residue. After filtration and concentration of the filtrate, the residue is chromatographed over silica gel (toluene/ethanol: 85/15), allowing the expected product to be isolated, which is converted into its fumarate form by the action of an ethanolic solution of fumaric acid.

Melting point: 118–120° C.

EXAMPLE 35

N-Methyl-1-[2-(3-pyridyloxy)ethyl]cyclopropanamine fumarate

Step 1: tert-Butyl methyl{1-[2-(3-pyridyloxy)ethyl]cyclopropyl}carbamate

To a solution of 1.7 g of triphenylphosphine and 0.6 g of 3-hydroxypyridine in 25 ml of tetrahydrofuran there are added, in succession, 1.3 g of the compound of Preparation Q and 1.35 g of diisopropyl azodicarboxylate. After reacting for 20 hours at ambient temperature, the mixture is concentrated and then taken up in ether and extracted with 1N hydrochloric acid. After customary treatment, the organic phases are evaporated under reduced pressure. Chromatography over silica gel (dichloromethane/tetrahydrofuran: 97/3) allows the expected product to be isolated.

Step 2: N-Methyl-1-[2-(3-pyridyloxy)ethyl]cyclopropanamine fumarate

A solution of 1.2 g of the product obtained in Step 1 dissolved in 5 ml of dioxane and 4 ml of 4N hydrochloric acid in dioxan is stirred for 20 hours at ambient temperature and then 10 ml of ether are added. The precipitate formed is separated off, taken up in 15 ml of water and made alkaline by the addition of potassium carbonate. The aqueous phase is then extracted with dichloromethane. The organic phases are subjected to customary treatment which, after concentration under reduced pressure, allows the expected product to be obtained, which is converted into its fumarate form by treatment with an ethanolic solution of fumaric acid.

Melting point: 110–112° C.

EXAMPLE 36

2-[1-(Methylamino)cyclopropyl]ethyl dimethylcarbamate hydrochloride

Step 1: 2-{1-[(tert-Butoxycarbonyl)(methyl)amino]cyclopropyl}ethyl dimethylcarbamate The product is obtained according to the procedure of Example 11 using as substrate the compound of Preparation Q.

Step 2: 2-[1-(Methylamino)cyclopropyl]ethyl dimethylcarbamate hydrochloride

The product is obtained according to the procedure of Example 18 Step 2 using as substrate the compound obtained in the previous Step.

Melting point: 104–108° C.

EXAMPLE 37

2-[1-(1-Pyrrolidinyl)cyclopropyl]ethyl dimethylcarbamate fumarate

The product is obtained according to the procedure of Example 36 using as substrate the compound of Preparation R.

Melting point: 108–110° C.

PHARMACOLOGICAL STUDIES OF COMPOUNDS OF THE INVENTION

EXAMPLE 38

Displacement of Binding of [$^{125}$I]-α-bungarotoxin on Nicotinic Receptors of the Electric Organ of Torpedo Fish This study, carried out according to the method described in J. Pharmacol. Exp. Ther., 1994, 271 624–631, is aimed at assessing the affinity of compounds of the present invention for nicotinic receptors of the "muscular" type. Membranes (1–5 μg/ml) of the electric organ of torpedo fish are incubated (1 hour, 22° C.) in the presence of a series of concentrations (0.01–10 μM) of each compound of the invention (diluted starting from a 10 mM stock solution in DMSO) in the presence of [$^{125}$I]-α-bungarotoxin (S.A.: 7.4 TBq/mmol: 0.2 nM) in Krebs buffer (Tris-HCl 50 mM, KCl 5 mM, MgCl$_2$ 1 mM, CaCl$_2$ 2 mM, NaCl 100 mM, pH 7.4) with 0.01% BSA; final volume: 500 μl. The non-specific binding is determined by incubating membranes in the presence of α-bungarotoxin (1 μM).

The results show that, up to a concentration of 10 μM, the compounds of the present invention have no significant affinity for nicotinic receptors of the "muscular" type.

EXAMPLE 39

Displacement of Binding of [$^3$H]-epibatidine on Nicotinic Receptors of IMR32 Cells This study, carried out according to the technique described in Molec. Pharmacol., 1995, 48; 280–287, is aimed at determining the affinity of compounds of the present invention for nicotinic receptors of the "ganglionic" type (American Soc. Neuroscience, 2000, 26, 138).

Membranes (250 μg/ml) of IMR-32 neuroblastoma cells are incubated (2 hours, 20° C.) in the presence of a series of concentrations (0.01–10 μM) of each compound of the invention (diluted starting from a 10 mM stock solution in DMSO) and (±)-[$^3$H]-epibatidine (S.A.: 2464 GBq/mmol:

1.5 nM) in phosphate buffer (NaH$_2$PO$_4$ 20 mM, pH 7.4); final volume: 250 μl. The non-specific binding is determined by incubating membranes in the presence of 300 μM of (−)nicotine.

The results show that, up to a concentration of 10 μM, the compounds of the present invention have no significant affinity for nicotinic receptors of the "ganglionic" type.

EXAMPLE 40

Displacement of Binding of [$^3$H]-oxotremorine-M on Muscarinic Receptors of Rat Brain This study, carried out according to the method described in Naumyn-Schmiederberg's Arch. Pharmacol., 2001, 363, 429–438, is aimed at determining the affinity of compounds of the present invention for muscarinic receptors.

Membranes (250 μg/ml) of rat brain are incubated (2 hours, 20° C.) in the presence of a series of concentrations (0.01–10 μM) of each compound of the invention (diluted starting from a 10 mM stock solution in DMSO) and [$^3$H]-oxotremorine-M (S.A.: 3174 GBq/mmol: 2 nM) in phosphate buffer (NaH$_2$PO$_4$ 20 mM, pH 7.4); final volume: 250 μl. The non-specific binding is determined by incubating membranes in the presence of atropine (1 μM). The affinity of the compounds of the present invention for muscarinic receptors is characterised by determination of the K$_i$.

The results show that, up to a concentration of 10 μM, most of the compounds of the present invention have no affinity for muscarinic receptors. Certain compounds of the invention have a K$_i$ of the order of 10 μM.

EXAMPLE 41

Displacement of Binding of [$^{125}$I]-α-bungarotoxin on "Type α7" Nicotinic Receptors of Rat Brain This study, carried out according to the method described in Molec. Pharmacol., 1986, 30; 427–436, is aimed at determining the affinity of compounds of the present invention for type α7 central nicotinic receptors.

Membranes (1000 μg/ml) of rat brain are incubated (5 hours, 37° C.) in the presence of a series of concentrations (0.01–10 μM) of each compound of the present invention (diluted starting from a 10 mM stock solution in DMSO) and [$^{125}$I]-α-bungarotoxin (S.A.: 7.4 TBq/mmol:1 nM) in Krebs buffer (Tris-HCl 50 mM, KCl 5 mM, MgCl$_2$ 1 mM, CaCl$_2$ 2 mM, NaCl 100 mM, pH 7.4) with 0.05% BSA; final volume: 500 gl. The non-specific binding is determined by incubating membranes in the presence of α-bungarotoxin (1 μM). The affinity of compounds of the present invention for type α7 nicotinic receptors is characterised by determination of the K$_i$.

The results show that, up to a concentration of 10 μM, most of the compounds of the present invention have no affinity for type α7 central nicotinic receptors. Certain compounds of the invention have a K$_i$ of the order of 10 μM.

EXAMPLE 42

Displacement of Binding of [$^3$H]-cytisine on "Type α4β2" Nicotinic Receptors of Rat Brain This study, carried out according to the technique described in Molec. Pharmacol., 1990, 39; 9–12, is aimed at determining the affinity of compounds of the present invention for type α4β2 central nicotinic receptors. Membranes (250 μg/ml) of rat brain are incubated (2 hours, 20° C.) in the presence of a series of concentrations (0.01–10 μM) of each compound of the present invention (diluted starting from a 10 mM stock solution in DMSO) and [$^3$H]-cytisine (S.A.: 1184 GBq/mmol: 2 nM) in phosphate buffer (NaH$_2$PO$_4$ 20 mM, pH 7.4); final volume: 250 μl. The non-specific binding is determined by incubating membranes in the presence of 10 μM of (−)nicotine. The affinity of the compounds of the present invention for type α4β2 central nicotinic receptors is characterised by determination of the K$_i$. The results obtained show that the compounds of the present invention have a strong affinity for type α4β2 central nicotinic receptors of the order of 10–100 nM.

These results, and also those obtained in Examples 39 to 42, show that the compounds of the present invention are powerful central nicotinic ligands that are specific to type α4β2 receptors.

EXAMPLE 43

In vivo Measurement of the Release of Acetylcholine by Means of Intra-cortical Microdialysis in the Conscious Wistar Rat The systemic administration of nicotine and nicotinic agonists causes an increase, in vivo, of acetylcholine in various regions of the brain (Neurochem. Res., 1996, 21, 1181–1186; Eur. J. Pharmacol., 1998, 351, 181–188; Br. J. Pharmacol., 1999, 127, 1486–1494). A microdialysis probe is implanted in the median prefrontal cortex of male Wistar rats. Six or seven days after they have been implanted, the probes are perfused with Ringer's solution (NaCl 147 mM, KCl 2.7 mM, CaCl$_2$ 1.2 mM, MgCl$_2$ 1 mM, neostigmine 20 nM) at a flow rate of 1 μl/min, the animal being free to move. After 2 hours in the animal quarters, the product under test is administered by the intraperitoneal route. A group of control animals receives the solvent used for the product. The dialysates (30 μl) are then collected every 30 minutes for 4 hours in order to measure the cortical extra-synaptic concentrations of acetylcholine by means of HPLC with amperometric detection. The results are expressed in pg of acetylcholine/dialysate, and inter-group comparisons are carried out by means of analysis of variance using 2 factors (treatment×time), with measurements being repeated over time.

The results obtained show that the compounds of the present invention increase, in vivo, the cortical release of acetylcholine in a dose-dependent manner (+74% to +138%) for doses ranging from 0.3 to 3 mg/kg IP, indicating the α4β2-agonist character of the compounds of the present invention.

EXAMPLE 44

Abdominal Contractions Induced by Phenyl-p-benzoquinone (PBQ) in the NMRI Mouse

Intraperitoneal administration of an alcoholic solution of PBQ causes abdominal cramps in the mouse (Proc. Soc. Exp. Biol., 1957, 95, 729–731). The cramps are characterised by repeated contractions of the abdominal musculature, accompanied by extension of the hind limbs. Most analgesics antagonise these abdominal cramps (Brit. J. Pharmacol. Chem., 1968, 32, 295–310). At t=0 min., the animals are weighed and the compound being studied is administered by the IP route. A group of control animals is given the solvent used for the compound. At t=30 min., an alcoholic solution of PBQ (0.2%) is administered by the IP route in a volume of 0.25 ml/mouse. Immediately after administration of the PBQ, the animals are placed in cylinders of plexiglass (L=19.5 cm; I.D.=5 cm). From t=35 min. to t=45 min., the animals' reaction is observed and the experimenter notes the total number of abdominal cramps per animal. The results are expressed as the percentage inhibition of the number of abdominal cramps measured in the control animals, at the active dose of the compound studied.

The results obtained show inhibition ranging from 50 to 80% for active doses ranging from 3 to 20 mg/kg IP, which shows that the compounds of the invention possess antalgic properties.

EXAMPLE 45

Social Recognition in the Wistar Rat

Initially described in 1982 (J. Comp. Physiol., 1982, 96, 1000–1006), the social recognition test has subsequently been proposed by various authors (Psychopharmacology, 1987, 91, 363–368; Psychopharmacology, 1989, 97, 262–268) for studying the mnemocognitive effects of new compounds. The test is based on the natural expression of the olfactory memory of the rat and its natural tendency to forget and allows evaluation of memorisation, by recognition of a young congeneric animal, by an adult rat. A young rat (21 days), taken at random, is placed for 5 minutes in the cage housing an adult rat. With the aid of a video device, the experimenter observes the social recognition behaviour of the adult rat and measures its overall duration. The young rat is then removed from the adult rat's cage and is placed in its own cage until the second introduction. The adult rat is given the compound under test and, after 2 hours, is again brought into the presence (5 minutes) of the young rat. The social recognition behaviour is then observed again and its duration measured. The assessment criterion is the difference (T2–T1), expressed in seconds, between the "recognition" times of the 2 encounters.

The results obtained show a difference (T2–T1) ranging from –31 s to –45 s for doses ranging from 1 to 3 mg/kg IP, which shows that the compounds of the invention very greatly enhance memorisation, even at a low dose.

EXAMPLE 46

Object Recognition in the Wistar Rat

The object recognition test in the Wistar rat (Behav. Brain Res., 1988, 31, 47–59) is based on the spontaneous exploratory activity of the animal and has the characteristics of episodic memory in humans. This memory test is sensitive to ageing (Eur. J. Pharmacol., 1997, 325, 173–180) and to cholinergic dysfunctions (Pharm. Biochem. Behav. 1996, 53(2), 277–283) and is based on the differences in the exploration of 2 objects of fairly similar shape—one familiar, the other new. Prior to the test, the animals are habituated to the environment (an enclosure without an object). In the course of a first session, the rats are placed (3 minutes) in the enclosure, in which there are 2 identical objects. The duration of exploration is measured for each object. In the course of the second session (3 minutes), 24 hours later, 1 of the 2 objects is replaced by a new object. The duration of exploration is measured for each object. The assessment criterion is the difference, Delta, expressed in seconds, between the exploration times for the new object and for the familiar object in the course of the second session. The control animals, previously treated with the carrier by the oral route 60 minutes before each session, explore the familiar object and the new object in an identical manner, which indicates that the object introduced earlier has been forgotten. Animals treated with a compound that facilitates mnemocognition preferentially explore the new object, which indicates that the object introduced earlier has been remembered. The results obtained show a difference, Delta, of the order of 6 s, for doses ranging from 0.3 to 1 mg/kg PO, which shows that the compounds of the invention greatly enhance memorisation, even at a very low dose.

EXAMPLE 47

Pharmaceutical Compositions for 1000 Tablets each Containing 10 mg of Active Ingredient

| | |
|---|---|
| Compound of Example 18 | 10 g |
| Hydroxypropyl methylcellulose | 10 g |
| Wheat starch | 15 g |
| Lactose | 90 g |
| Magnesium stearate | 2 g |

What is claimed is:

1. A compound selected from those of formula (I):

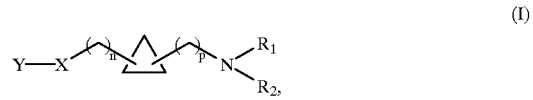

(I)

wherein:

p represents an integer of from 0 to 6 inclusive, n represents an integer of from 0 to 6 inclusive, $R_1$ and $R_2$, which may be identical or different, each independently of the other represent a group selected from hydrogen, linear or branched ($C_1$–$C_6$)alkyl, aryl, and aryl-($C_1$–$C_6$)alkyl in which alkyl is linear or branched, X represents a group selected from oxygen, sulfur, Y represents pyridyl, its isomer and addition salts thereof with a pharmaceutically-acceptable acid or base, it also being understood that:

aryl denotes phenyl, biphenyl, naphthyl, dihydronaphthyl, tetrahydronaphthyl, indanyl, or indenyl, each of those groups being optionally substituted by one or more, identical or different, groups selected from halogen, linear or branched ($C_1$–$C_6$) alkyl, hydroxy, cyano, nitro, linear or branched ($C_1$–$C_6$)alkoxy, linear or branched($C_2$–$C_7$)acyl, linear or branched ($C_1$–$C_6$)alkoxycarbonyl, linear or branched ($C_1$–$C_6$)trihaloalkyl, linear or branched ($C_1$–$C_6$)trihaloalkoxy, and amino optionally substituted by one or two linear or branched ($C_1$–$C_6$)alkyl, pyridyl denotes a pyridyl group which is optionally substituted by one or more, identical or different, groups selected from substituents defined hereinbefore for aryl.

2. A compound of claim 1, wherein n is an integer of from 0 to 2 inclusive.

3. A compound of claim 1, wherein $R_1$, and R2, which may be identical or different, each represent hydrogen, or linear or branched ($C_1$–$C_6$)alkyl.

4. A compound of claim 1 wherein X represents oxygen.

5. A compound of claim 1, Which is a compound of formula (IA):

(IA)

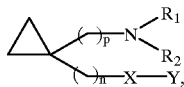

wherein n, p, X, Y, $R_1$ and R2 are as defined for formula (I), its isomers and addition salts thereof with a pharmaceutically-acceptable acid or base.

6. A compound of claim 1, which is a compound of formula (IB):

(IB)

wherein n, p, X, Y, $R_1$, and $R_2$ are as defined for formula (I), its isomers and addition salts thereof with a pharmaceutically-acceptable acid or base.

7. A compound of claim 1, wherein p is an integer having the value 0 or 1.

8. A compound of claim 7, wherein p represents 0, or 1, n represents 0, or 1, $R_1$ and $R_2$, which may be identical or different, represent hydrogen, or linear or branched ($C_1$–$C_6$) alkyl, X represents oxygen, and Y represents pyridyl, its isomers and addition salts thereof with a pharmaceutically-acceptable acid or base.

9. A compound of claim 5, wherein p represents 0, or 1, n is an integer of from 0 to 3 inclusive, $R_1$ and $R_2$, which may be identical or different, represent hydrogen, linear or branched ($C_1$–$C_6$)alkyl, X represents oxygen or sulphur and Y represents pyridyl, (pyridyl being optionally substituted by a group selected from halogen, and linear or branched ($C_1$–$C_6$)alkyl), its isomers and addition salts thereof with a pharmaceutically-acceptable acid or base.

10. A compound of claim 1, which is selected from:
N,N-dimethyl-1-[(3-pyridyloxy)methyl]cyclopropanamine,
N-methyl-1-[(3-pyridyloxy)methyl]cyclopropanamine,
N,N-dimethyl-1-[(3-pyridylmethoxy)methyl]cyclopropanamine,
N,N-dimethyl-1-[2-(3-pyridyloxy)ethyl]cyclopropanamine,
1-[(3-pyridyloxy)methyl]cyclopropanamine dihydrochloride,
N-methyl-1-{[(6-methyl-3-pyridyl)oxy]methyl}cyclopropanamine hydrochloride,
N-methyl-1-{[(6-chloro-3-pyridyl)oxy]methyl}cyclopropanamine hydrochloride,
N-methyl-1-[2-pyridylsulphanyl)methyl]cyclopropanamine dihydrochloride,
N-methyl-1-[3-(3-pyridyloxy)propyl]cyclopropanamine dihydrochloride, and
N-methyl-1-[2-(3-pyridyloxy)ethyl]cyclopropanamine fumarate,
its isomers and addition salts thereof with a pharmaceutically-acceptable sold or base.

11. A pharmaceutical composition comprising as active principle an effective amount of a compound as claimed in claim 1, alone or in combination with one or more pharmaceutically-acceptable excipients or carriers.

12. A method for treating pain and memory or cognitive deficiency in a living animal body afflicted with age related cognitive disorders and neurodegenerative disorders selected from Alzheimer's disease, Parkinson's disease, Pick's disease, Korsakoff's disease, frontal lobe and sub-cortical dementias, attention-deficit disorder, comprising the step of administering to the living animal body an amount of a compound of claim 1 which is effective for alleviation of said conditions.

* * * * *

UNITED STATES PATENT AND TRADEMARK OFFICE
CERTIFICATE OF CORRECTION

PATENT NO. : 6,943,184 B2
DATED : September 13, 2005
INVENTOR(S) : Solo Goldstein et al.

It is certified that error appears in the above-identified patent and that said Letters Patent is hereby corrected as shown below:

Title page,
Item [73], Assignee, "Les Laboratories Servier" should be -- Les Laboratoires Servier --.
Item [56], References Cited, OTHER PUBLICATIONS,
"Neuropsychopharmacology, 22, 461-565" should be -- Neuropsychopharmacology, 22, 451-565 --; and,
"Am. J. Psychiatry, 160" should be -- Am. J. Psychiatry, 150 --.

Column 43,
Line 8, "R2" should be -- $R_2$ --.
Line 25, "claim 7" should be -- claim 6 --.

Column 44,
Line 16, "[2-pyridylsulphanyl)methyl]" should be -- [(2-pyridylsulphanyl)methyl] --.

Signed and Sealed this

Twenty-seventh Day of December, 2005

JON W. DUDAS
*Director of the United States Patent and Trademark Office*